United States Patent
Yagi et al.

(10) Patent No.: US 11,467,489 B2
(45) Date of Patent: Oct. 11, 2022

(54) ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

(71) Applicant: FUJIFILM Corporation, Tokyo (JP)

(72) Inventors: Kazunari Yagi, Haibara-gun (JP); Takashi Kawashima, Haibara-gun (JP); Tomotaka Tsuchimura, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/805,922

(22) Filed: Mar. 2, 2020

(65) Prior Publication Data

US 2020/0201177 A1    Jun. 25, 2020

Related U.S. Application Data

(63) Continuation of application No. PCT/JP2018/031691, filed on Aug. 28, 2018.

(30) Foreign Application Priority Data

Sep. 20, 2017  (JP) .............................. JP2017-180109

(51) Int. Cl.
*G03F 7/004* (2006.01)
*G03F 7/11* (2006.01)
*G03F 7/20* (2006.01)

(52) U.S. Cl.
CPC .......... *G03F 7/0045* (2013.01); *G03F 7/0046* (2013.01); *G03F 7/11* (2013.01); *G03F 7/2041* (2013.01)

(58) Field of Classification Search
CPC ........ G03F 7/0045; G03F 7/0046; G03F 7/11; G03F 7/2041; G03F 7/039; G03F 7/027; G03F 7/0392; G03F 7/0397; G03F 7/0388; G03F 7/038; G03F 7/004; C07D 307/93; C07D 321/12; C07D 307/64; C07D 311/74; C07D 237/16; C07D 327/04; C07D 295/185; C07D 307/94; C07D 237/04; C07D 493/10; C07D 311/20; C07D 319/06; C07D 307/60; C07D 313/06; C07D 211/46; C07D 207/416; C07D 295/18; C07D 317/24; C07D 307/33; C07C 309/27; C07C 309/18; C07C 309/17; C07C 381/12; C07C 2601/08; C07C 2603/74; C07C 2601/14; C07C 2601/18; C07C 2601/10; C07C 309/12
See application file for complete search history.

(56) References Cited

U.S. PATENT DOCUMENTS

| | | | |
|---|---|---|---|
| 2014/0363769 A1 | 12/2014 | Namai et al. | |
| 2015/0004545 A1* | 1/2015 | Namai | C07D 295/185 430/285.1 |
| 2015/0168829 A1* | 6/2015 | Domon | C07C 309/43 430/296 |

FOREIGN PATENT DOCUMENTS

| | | |
|---|---|---|
| JP | 2013-250433 A | 12/2013 |
| JP | 2014-152122 A | 8/2014 |
| JP | 2014-224984 A | 12/2014 |
| JP | 2017-102267 A | 6/2017 |
| JP | 2017-156650 A | 9/2017 |
| TW | 201403222 A | 1/2014 |
| WO | 2013/129266 A1 | 9/2013 |
| WO | 2013/140969 A1 | 9/2013 |
| WO | 2014/034190 A1 | 3/2014 |

OTHER PUBLICATIONS

English Translation of JP 2017-156650 A; Hayato Namai; Published: Sep. 7, 2017 (Year: 2017).*
International Search Report dated Nov. 6, 2018, issued by the International Searching Authority in application No. PCT/JP2018/031691.
Written Opinion dated Nov. 6, 2018, issued by the International Searching Authority in application No. PCT/JP2018/031691.
International Preliminary Report on Patentability dated Mar. 24, 2020, issued by the International Bureau in application No. PCT/JP2018/031691.
Communication dated Jan. 26, 2021, from the Japanese Patent office, in Japanese Application No. 2019-543505.
Office Action dated Oct. 5, 2021 in Korean Application No. 10-2020-7006375.
Communication dated Feb. 25, 2022 from the Taiwanese Patent Office in Taiwanese Application No. 107130904.

* cited by examiner

*Primary Examiner* — Peter L Vajda
*Assistant Examiner* — Richard David Champion
(74) *Attorney, Agent, or Firm* — Sughrue Mion, PLLC

(57) ABSTRACT

An actinic ray-sensitive or radiation-sensitive resin composition contains a compound that generates an acid upon irradiation with actinic rays or radiation and a resin whose polarity increases by the action of an acid, in which the compound is represented by a specific General Formula (X).

21 Claims, No Drawings

ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

CROSS-REFERENCE TO RELATED APPLICATIONS

This application is a Continuation of PCT International Application No. PCT/JP2018/31691, filed on Aug. 28, 2018, which claims priority under 35 U.S.C. § 119(a) to Japanese Patent Application No. 2017-180109, filed on Sep. 20, 2017. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition, a resist film, a pattern forming method, and a method for manufacturing an electronic device.

2. Description of the Related Art

In processes for manufacturing semiconductor devices such as an integrated circuit (IC) and a large scale integrated circuit (LSI) in the related art, microfabrication by lithography using a photoresist composition (hereinafter also referred to as an "actinic ray-sensitive or radiation-sensitive resin composition") has been performed. In recent years, formation of an ultrafine pattern in a submicron region or a quarter-micron region has been demanded in accordance with realization of a high degree of integration for integrated circuits. With such a demand, a tendency that an exposure wavelength has been shifted from g-rays to i-rays, and further, as with KrF excimer laser light, the exposure wavelength becomes shorter is observed. Moreover, developments in lithography with electron beams, X-rays, or extreme ultraviolet rays (EUV), in addition to the excimer laser light, have also been currently proceeding.

WO2013/129266A and WO2014/034190A each disclose an actinic ray-sensitive or radiation-sensitive resin composition which can be applied to EUV exposure and the like.

SUMMARY OF THE INVENTION

In recent years, performance required for an actinic ray-sensitive or radiation-sensitive resin composition has become higher.

The present inventors have examined the actinic ray-sensitive or radiation-sensitive resin compositions described in WO2013/129266A and WO2014/034190A. As a result, it was clarified that the compositions have insufficient line edge roughness (LER) in some cases.

Therefore, an object of the present invention is to provide an actinic ray-sensitive or radiation-sensitive resin composition having excellent LER In addition, another object of the present invention is to provide a resist film, a pattern forming method, and a method for manufacturing an electronic device, each using the actinic ray-sensitive or radiation-sensitive resin composition.

The present inventors have conducted extensive studies and as a result, they have found that the objects can be accomplished by using an actinic ray-sensitive or radiation-sensitive resin composition containing a specific photoacid generator, thereby completing the present invention.

That is, the present invention has an object to provide [1] to [13] below.

[1] An actinic ray-sensitive or radiation-sensitive resin composition comprising:
a compound that generates an acid upon irradiation with actinic rays or radiation; and
a resin whose polarity increases by the action of an acid,
in which the compound is represented by General Formula (X).

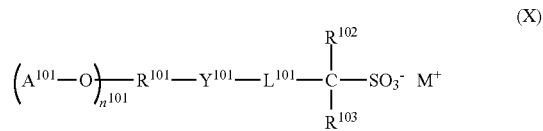

In General Formula (X).
$A^{101}$ represents a group that leaves by the action of an acid. In a case where a plurality of $A^{101}$'s are present, the plurality of $A^{101}$'s may be linked to each other.
$n^{101}$ represents an integer of 1 to 4.
$R^{101}$ represents an ($n^{101}$+1)-valent aliphatic hydrocarbon group having no heteroatom.
$Y^{101}$ represents an ether group or an ester group.
$L^{101}$ represents an alkylene group.
$R^{102}$ and $R^{103}$ each independently represent a hydrogen atom or an alkyl group having 1 to 10 carbon atom, in which a hydrogen atom is not substituted with a fluorine atom.
$M^+$ represents a monovalent cation.

[2] The actinic ray-sensitive or radiation-sensitive resin composition as described in [1],
in which the compound has an acetal structure or a ketal structure in a moiety including $A^{101}$ and $R^{101}$.

[3] The actinic ray-sensitive or radiation-sensitive resin composition as described in [1] or [2],
in which the compound is represented by General Formula (X-1).

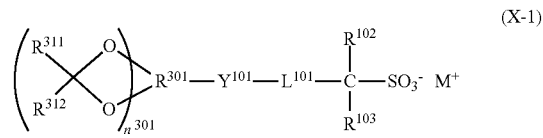

In General Formula (X-1),
$R^{311}$ and $R^{312}$ each independently represent a hydrogen atom, an alkyl group, an aryl group, a heteroaryl group, or a heterocyclic group.
$n^{301}$ represents an integer of 1 or 2.
$R^{301}$ represents an (($n^{301}$×2)+1)-valent aliphatic hydrocarbon group having no heteroatom.
$Y^{101}$ represents an ether group or an ester group.
$L^{101}$ represents an alkylene group.
$R^{102}$ and $R^{103}$ each independently represent a hydrogen atom or an alkyl group having 1 to 10 carbon atom, in which a hydrogen atom is not substituted with a fluorine atom.
$M^+$ represents a monovalent cation.

[4] The actinic ray-sensitive or radiation-sensitive resin composition as described in [3], in which $R^{301}$ represents an $((n^{301} \times 2)+1)$-valent alicyclic hydrocarbon group having no heteroatom.

[5] The actinic ray-sensitive or radiation-sensitive resin composition as described in [1] or [2],
in which the compound is represented by General Formula (X-2).

$$\left( R^{412} \underset{R^{413}}{\overset{OR^{411}}{\vert}} O \right)_{n^{401}} R^{401} - Y^{101} - L^{101} - \underset{R^{103}}{\overset{R^{102}}{\underset{\vert}{C}}} - SO_3^- \quad M^+ \quad (X-2)$$

In General Formula (X-2),
$R^{411}$ represents an alkyl group, an aryl group, a heteroaryl group, or a heterocyclic group.
$R^{412}$ and $R^{413}$ each independently represent a hydrogen atom, an alkyl group, an aryl group, a heteroaryl group, or a heterocyclic group.
$n^{401}$ represents an integer of 1 or 2.
$R^{401}$ represents an $(n^{401}+1)$-valent aliphatic hydrocarbon group having no heteroatom.
$Y^{101}$ represents an ether group or an ester group.
$L^{101}$ represents an alkylene group.
$R^{102}$ and $R^{103}$ each independently represent a hydrogen atom or an alkyl group having 1 to 10 carbon atom, in which a hydrogen atom is not substituted with a fluorine atom.
$M^+$ represents a monovalent cation.

[6] The actinic ray-sensitive or radiation-sensitive resin composition as described in any one of [1] to [5],
in which $Y^{101}$ represents an ether group.

[7] The actinic ray-sensitive or radiation-sensitive resin composition as described in any one of [1] to [6],
in which $M^+$ represents a substituted or unsubstituted triphenylsulfonium cation.

[8] The actinic ray-sensitive or radiation-sensitive resin composition as described in any one of [1] to [7],
in which the resin includes a repeating unit having an acid-decomposable group, the acid-decomposable group has a structure in which a polar group is protected with a group that leaves through decomposition by the action of an acid, and the polar group is a phenolic hydroxyl group.

[9] The actinic ray-sensitive or radiation-sensitive resin composition as described in any one of [1] to [8],
in which the resin includes a repeating unit having an acid-decomposable group, the acid-decomposable group has a structure in which a polar group is protected with a group that leaves through decomposition by the action of an acid, and the group that leaves through decomposition by the action of an acid is represented by Formula $-C(R_{01})(R_{02})(OR_{39})$,
in the formula. $R_{39}$ represents an alkyl group, a cycloalkyl group, an aryl group, an aralkyl group, or an alkenyl group, and $R_{01}$ and $R_{02}$ each independently represent a hydrogen atom, an alkyl group, a cycloalkyl group, an aryl group, an aralkyl group, or an alkenyl group.

[10] The actinic ray-sensitive or radiation-sensitive resin composition as described in any one of [1] to [9], further comprising a solvent.

[11] A resist film formed with the actinic ray-sensitive or radiation-sensitive resin composition as described in any one of [1] to [10].

[12] A pattern forming method comprising:
forming a resist film with the actinic ray-sensitive or radiation-sensitive resin composition as described in any one of [1] to [10];
exposing the resist film; and
developing the exposed resist film with a developer.

[13] A method for manufacturing an electronic device, the method comprising the pattern forming method as described in [12].

According to the present invention, it is possible to provide an actinic ray-sensitive or radiation-sensitive resin composition having excellent LER In addition, according to the present invention, it is possible to provide a resist film, a pattern forming method, and a method for manufacturing an electronic device, each using the actinic ray-sensitive or radiation-sensitive resin composition.

DESCRIPTION OF THE PREFERRED EMBODIMENTS

Hereinafter, the present invention will be described in detail.

Description of configuration requirements described below may be made on the basis of representative embodiments of the present invention in some cases, but the present invention is not limited to such embodiments.

"Actinic rays" or "radiation" in the present specification means, for example, a bright line spectrum of a mercury lamp, far ultraviolet rays typified by an excimer laser, extreme ultraviolet rays (EUV rays), X-rays, electron beams (EB), or the like. "Light" in the present specification means actinic rays or radiation.

"Exposure" in the present specification encompasses, unless otherwise specified, not only exposure by a bright line spectrum of a mercury lamp, far ultraviolet rays typified by an excimer laser, extreme ultraviolet rays (EUV rays), X-rays, or the like, but also lithography by particle rays such as electron beams and ion beams.

In the present specification, a numerical range expressed using "to" is used in a meaning of a range that includes the preceding and succeeding numerical values of "to" as the lower limit value and the upper limit value, respectively.

In the present specification, (meth)acrylate represents acrylate and methacrylate, and (meth)acrylic acid represents acrylic acid and methacrylic acid.

In citations for a group (atomic group) in the present specification, in a case where the group is cited without specifying whether it is substituted or unsubstituted, the group includes both a group having no substituent and a group having a substituent. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

Furthermore, in the present specification, in a case of referring to an expression "a substituent may be contained", the types of substituents, the positions of the substituents, and the number of the substituents are not particularly limited. The number of the substituents may be, for example, one, two, three, or more. Examples of the substituent include a monovalent non-metal atomic group from which a hydrogen atom has been excluded, and the substituent can be selected from the following substituent group T, for example.

Examples of the substituent T include halogen atoms such as a fluorine atom, a chlorine atom, a bromine atom, and an iodine atom an alkoxy group such as a methoxy group, an ethoxy group, and a tert-butoxy group; an aryloxy group such as a phenoxy group and a p-tolyloxy group; an alkoxycarbonyl group such as a methoxycarbonyl group, a butoxycarbonyl group, and a phenoxycarbonyl group; an acyloxy group such as an acetoxy group, a propionyloxy group, and a benzoyloxy group; an acyl group such as an acetyl group, a benzoyl group, an isobutyryl group, an acryloyl group, a methacryloyl group, and a methoxalyl group: an alkylsulfanyl group such as a methylsulfanyl group and a tert-butylsulfanyl group; an arylsulfanyl group such as a phenylsulfanyl group and a p-tolylsulfanyl group; an alkyl group: a cycloalkyl group; an aryl group; a heteroaryl group; a hydroxyl group; a carboxyl group; a formyl group; a sulfo group; a cyano group; an alkylaminocarbonyl group; an arylaminocarbonyl group; a sulfonamido group; a silyl group; an amino group; a monoalkylamino group; a dialkylamino group; an arylamino group; and a combination thereof.

[Actinic Ray-Sensitive or Radiation-Sensitive Resin Composition]

The actinic ray-sensitive or radiation-sensitive resin composition of an embodiment of the present invention (hereinafter also referred to as "the composition of the embodiment of the present invention") contains a compound that generates an acid upon irradiation with actinic rays or radiation, and a resin whose polarity increases by the action of an acid, in which the compound is represented by General Formula (X) which will be described later.

By adopting the configuration, the composition of the embodiment of the present invention is excellent in LER A reason therefor is not clear, but is presumed as follows.

In the compound represented by General Formula (X) (photoacid generator), a group represented by $A^{101}$ leaves by an acid itself generated upon irradiation with actinic rays or radiation and a hydrogen-bonding group such as a hydroxyl group appears. This hydrogen-bonding group interacts with a resin (for example, a carbonyl group and the like of the resin) around the hydrogen-bonding group, which thus suppresses acid diffusivity. As a result, it is presumed that LER is excellent.

At this time, it is presumed that an effect of suppressing acid diffusion is further improved by a configuration where in General Formula (X), $R^{101}$ has no heteroatom and $R^{102}$ and $R^{103}$ each represent a hydrogen atom or an alkyl group having 1 to 10 carbon atom, in which a hydrogen atom is not substituted with a fluorine atom.

For the same reason, it is presumed that the composition of the embodiment of the present invention is also excellent in an ability to suppress collapse of a pattern thus formed.

Hereinafter, the components included in the composition of the embodiment of the present invention will be described in detail. Furthermore, the composition of the embodiment of the present invention is a so-called resist composition, and may be either a positive-tone resist composition or a negative-tone resist composition. In addition, the composition of the embodiment of the present invention may be either a resist composition for alkali development or a resist composition for organic solvent development. Among those, the positive-tone resist composition which is the resist composition for alkali development is preferable.

The composition of the embodiment of the present invention is typically a chemically amplified resist composition.

<Compound that Generates Acid Upon Irradiation with Actinic Rays or Radiation>

The composition of the embodiment of the present invention contains a compound represented by General Formula (X) as described later, which generates an acid upon irradiation with actinic rays or radiation (hereinafter also referred to as a "photoacid generator").

The photoacid generator may be in a form of a low-molecular-weight compound or a form incorporated into a part of a polymer. Further, a combination of the form of a low-molecular-weight compound and the form incorporated into a part of a polymer may also be used.

In a case where the photoacid generator is in the form of a low-molecular-weight compound, the molecular weight is preferably 3,000 or less, more preferably 2,000 or less, and still more preferably 1.000 or less.

In a case where the photoacid generator is incorporated into a part of a polymer, it may be incorporated into a part of the resin (X) or in a resin other than the resin (X).

Among those, the photoacid generator is preferably in the form of a low-molecular-weight compound.

<<General Formula (X)>>

The photoacid generator is represented by General Formula (X).

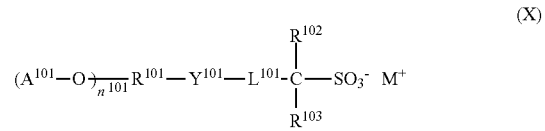

(X)

In General Formula (X).

$A^{101}$ represents a group that leaves by the action of an acid. In a case where a plurality of $A^{101}$'s are present, the plurality of $A^{101}$'s may be linked to each other.

$n^{101}$ represents an integer of 1 to 4.

$R^{101}$ represents an $(n^{101}+1)$-valent aliphatic hydrocarbon group having no heteroatom.

$Y^{101}$ represents an ether group or an ester group.

$L^{101}$ represents an alkylene group.

$R^{102}$ and $R^{103}$ each independently represent a hydrogen atom or an alkyl group having 1 to 10 carbon atom, in which a hydrogen atom is not substituted with a fluorine atom.

$M^+$ represents a monovalent cation.

Suitable examples of the group (leaving group) that leaves by the action of an acid, represented by $A^{101}$, include the same groups as a leaving group represented by Rc in General Formula (B-1) which will be described later.

The integer of 1 to 4 represented by $n^{101}$ is preferably an integer of 1 or 2.

Examples of the aliphatic hydrocarbon group represented by $R^{101}$ include a group formed by removing $n^{101}+1$ pieces of hydrogen atoms from an aliphatic hydrocarbon having no heteroatom. The number of carbon atoms of the aliphatic hydrocarbon group is, for example, 1 to 30, and preferably 2 to 15.

Examples of the aliphatic hydrocarbon having no heteroatom include a linear or branched aliphatic hydrocarbon such as methane, ethane, propane, butane, pentane, hexane, heptane, octane, nonane, decane, dodecane, and 2-ethylhexane; and an alicyclic hydrocarbon such as cyclohexane, t-butylcyclohexane, dicyclopentadiene, tricyclodecane, isobornyl, adamantane, and 2-methyl-2-adamantane.

More specific examples of the alicyclic hydrocarbon include a monocyclic hydrocarbon such as a cyclohexane ring, a cycloheptane ring, and a cyclooctane ring; a cross-linked cyclic hydrocarbon ring such as a norbonane ring, an adamantane ring, a bicyclooctane ring, and a tricyclo [5.2.1.0$^{2,6}$]decane ring; and a fused ring formed by fusing a plurality of 5- to 8-membered cycloalkane rings, such as a perhydronaphthalene (decalin) ring, a perhydroanthracene ring, a perhydrophenanthrene ring, a perhydroacenaphthene ring, a perhydrofluorene ring, a perhydroindene ring, and a perhydrophenalene ring.

As the aliphatic hydrocarbon group represented by $R^{101}$, a group formed by removing $n^{101}+1$ pieces of hydrogen atoms from an alicyclic hydrocarbon having no heteroatom is preferable for a reason that LER is more excellent.

$Y^{101}$ represents an ether group (—O—) or an ester group (—O—CO—).

For a reason that LER and resistance to pattern collapse are more excellent, an ether group is preferable as $Y^{101}$.

Examples of the alkylene group represented by $L^{101}$ include an alkylene group having 1 to 8 carbon atoms, such as a methylene group, an ethylene group, a propylene group, a butylene group, a hexylene group, and an octylene group, and the alkylene group is preferably an alkylene group having 1 to 4 carbon atoms.

It is preferable that a hydrogen atom in the alkylene group represented by $L^{101}$ is not substituted with a fluorine atom.

Examples of the alkyl group having 1 to 10 carbon atom, represented by each of $R^{102}$ and $R^{103}$, in which a hydrogen atom is not substituted with a fluorine atom, include a methyl group, an ethyl group, a propyl group, an isopropyl group, a butyl group, an isobutyl group, a tert-butyl group, a pentyl group, a hexyl group, a cyclohexyl group, a heptyl group, a 3-heptyl group, an octyl group, a 2-ethylhexyl group, a nonyl group, and a decyl group, and the alkyl group is preferably an alkyl group having 1 to 5 carbon atoms, and more preferably an alkyl group having 1 to 3 carbon atoms.

As each of $R^{102}$ and $R^{103}$, a hydrogen atom is preferable.

The monovalent cation represented by M$^+$ will be described later.

The photoacid generator represented by General Formula (X) preferably has an acetal structure or a ketal structure in a moiety including $A^{101}$ and $R^{101}$ as described above. Examples of such a photoacid generator having the acetal structure or the ketal structure include a photoacid generator represented by General Formula (X-1) which will be described later.

Examples of the photoacid generator represented by General Formula (X) include a photoacid generator represented by General Formula (X-1) or General Formula (X-2).

Among those, the photoacid generator represented by General Formula (X-1) is preferable for a reason that LER is more excellent.

<<General Formula (X-1)>>

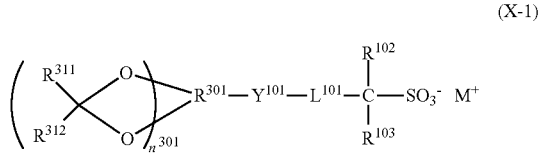

(X-1)

In General Formula (X-1).

$R^{311}$ and $R^{312}$ each independently represent a hydrogen atom, an alkyl group, an aryl group, a heteroaryl group, or a heterocyclic group.

$n^{301}$ represents an integer of 1 or 2.

$R^{301}$ represents an (($n^{301}\times2$)+1)-valent aliphatic hydrocarbon group having no heteroatom.

$Y^{101}$ represents an ether group or an ester group.

$L^{101}$ represents an alkylene group.

$R^{102}$ and $R^{103}$ each independently represent a hydrogen atom or an alkyl group having 1 to 10 carbon atom, in which a hydrogen atom is not substituted with a fluorine atom.

M$^+$ represents a monovalent cation.

$Y^{101}$, $L^{101}$, $R^{102}$, $R^{103}$, and M$^+$ in General Formula (X-1) have the same definitions as $Y^{101}$, $L^{101}$, $R^{102}$, $R^{103}$, and M$^+$, respectively, in General Formula (X) as described above.

Examples of the alkyl group represented by each of $R^{311}$ and $R^{312}$ include a linear, branched, or cyclic alkyl group having 1 to 10 carbon atoms, such as a methyl group, an ethyl group, a propyl group, an isopropyl group, a butyl group, an isobutyl group, a tert-butyl group, a pentyl group, a hexyl group, a cyclohexyl group, a heptyl group, a 3-heptyl group, an octyl group, a 2-ethylhexyl group, a nonyl group, and a decyl group, and the alkyl group is preferably an alkyl group having 1 to 6 carbon atoms.

In a case where the alkyl group represented by each of $R^{311}$ and $R^{312}$ is a linear or branched alkyl group, the alkyl group may have a heteroatom such as an oxygen atom.

The aryl group represented by each of $R^{311}$ and $R^{112}$ is not particularly limited, examples thereof include an aryl group having 6 to 18 carbon atoms, such as a phenyl group and a naphthyl group, and the aryl group is preferably an aryl group having 6 to 14 carbon atoms.

Examples of the heteroaryl group represented by each of $R^{311}$ and $R^{312}$ include a group derived from a monocyclic or polycyclic aromatic ring containing a heteroatom such as a nitrogen atom, an oxygen atom, and a sulfur atom. Specific examples of the monocyclic or polycyclic aromatic ring containing a heteroatom include thiophene, furan, pyrrole, pyrazole, imidazole, triazole, oxazole, thiazole, pyridine, pyrazine, pyrimidine, and pyridazine.

Examples of the heterocyclic group represented by each of $R^{311}$ and $R^{312}$ include a group derived from a monocyclic or polycyclic alicyclic hydrocarbon containing a heteroatom such as a nitrogen atom, an oxygen atom, and a sulfur atom. Specific examples of the monocyclic or polycyclic alicyclic hydrocarbon containing a heteroatom include tetrahydrofuran, tetrahydropyran, morpholine, thiomorpholine, piperidine, and pyrrolidine.

As each of $R^{311}$ and $R^{312}$, the alkyl group or the aryl group is preferable.

$n^{301}$ represents an integer of 1 or 2, and is preferably an integer of 1.

Examples of the aliphatic hydrocarbon group represented by $R^{301}$ include a formed by removing ($n^{301}\times2$)+1 pieces of hydrogen atoms from an aliphatic hydrocarbon having no heteroatom.

Suitable examples of the aliphatic hydrocarbon having no heteroatom in $R^{301}$ include the aliphatic hydrocarbon having no heteroatom described for $R^{101}$ in General Formula (X) as described above.

For a reason that LER is further excellent, it is preferable that $R^{301}$ represents an (($n^{301}\times2$)+1)-valent alicyclic hydrocarbon group having no heteroatom. For example, $R^{301}$ is preferably a group formed by removing ($n^{301}\times2$)+1 pieces of hydrogen atoms from an alicyclic hydrocarbon such as cyclohexane, t-butylcyclohexane, dicyclopentadiene, tricyclodecane, isobornyl, adamantane, and 2-methyl-2-adamantane.

<<General Formula (X-2)>>

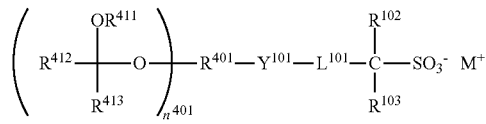

(X-2)

In General Formula (X-2), $R^{411}$ represents an alkyl group, an aryl group, a heteroaryl group, or a heterocyclic group.

$R^{412}$ and $R^{413}$ each independently represent a hydrogen atom, an alkyl group, an aryl group, a heteroaryl group, or a heterocyclic group.

$n^{401}$ represents an integer of 1 or 2.

$R^{401}$ represents an ($n^{401}$+1)-valent aliphatic hydrocarbon group having no heteroatom.

$Y^{101}$ represents an ether group or an ester group.

$L^{101}$ represents an alkylene group.

$R^{102}$ and $R^{103}$ each independently represent a hydrogen atom or an alkyl group having 1 to 10 carbon atom, in which a hydrogen atom is not substituted with a fluorine atom.

$M^+$ represents a monovalent cation.

$Y^{101}$, $L^{101}$, $R^{102}$, $R^{103}$, and $M^+$ in General Formula (X-2) have the same definitions as $Y^{101}$, $L^{101}$, $R^{102}$, $R^{103}$, and $M^+$, respectively, in General Formula (X) as described above.

The alkyl group, the aryl group, the heteroaryl group, and the heterocyclic group represented by each of $R^{411}$, $R^{412}$, and $R^{413}$ have the same definitions as the alkyl group, the aryl group, the heteroaryl group, and the heterocyclic group represented by each of $R^{311}$ and $R^{312}$, respectively, in General Formula (X-1) as described above.

As each of $R^{411}$, $R^{412}$, and $R^{413}$, the alkyl group or the aryl group is preferable.

$n^{401}$ represents an integer of 1 or 2, and is preferably an integer of 2.

Examples of the aliphatic hydrocarbon group represented by $R^{401}$ include a group formed by removing $n^{401}$+1 pieces of hydrogen atoms from an aliphatic hydrocarbon having no heteroatom.

Suitable examples of the aliphatic hydrocarbon having no heteroatom in $R^{401}$ include the aliphatic hydrocarbon having no heteroatom described for $R^{101}$ General Formula (X) as described above.

For a reason that LER is more excellent, it is preferable that $R^{401}$ represents an ($n^{401}$+1)-valent alicyclic hydrocarbon group having no heteroatom.

<<Specific Examples of Anionic Moiety>>

Specific examples of the anionic moiety of the photoacid generator represented by General Formula (X) (including General Formula (X-1) and General Formula (X-2)) are shown below. It should be noted that the present invention is not particularly limited to specific examples shown below

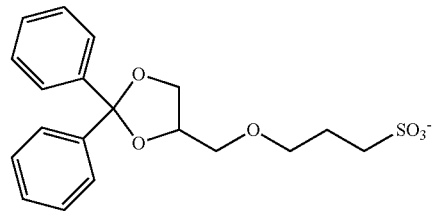
(A001)

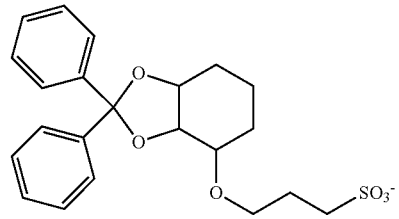
(A002)

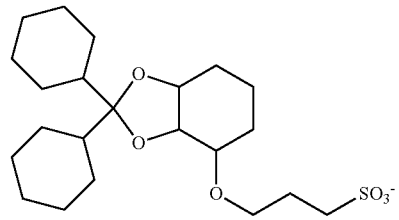
(A003)

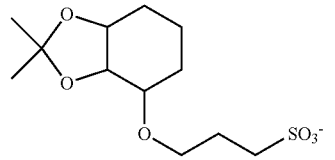
(A004)

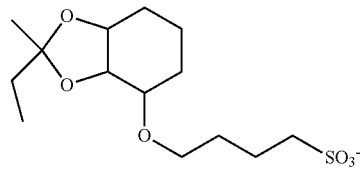
(A005)

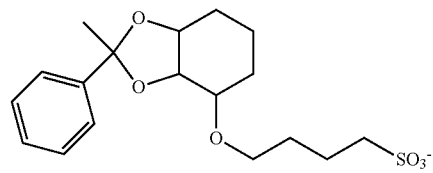
(A006)

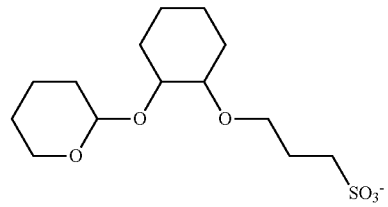
(A007)

(A008) 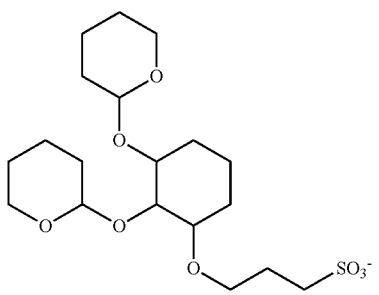
(A009) 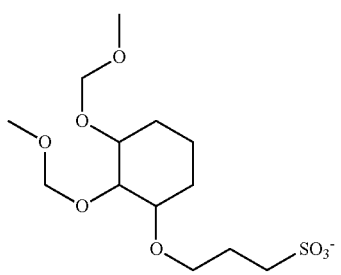
(A010) 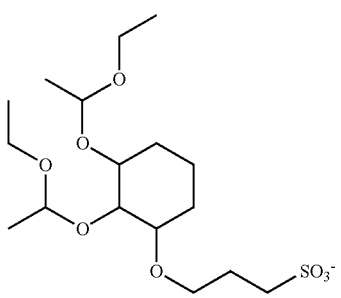
(A011) 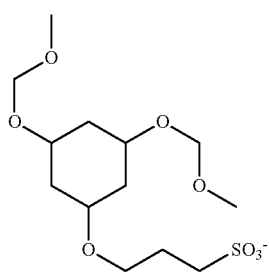
(A012) 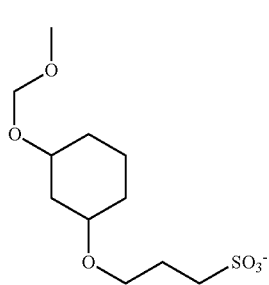
(A013) 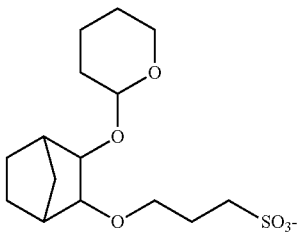
(A014) 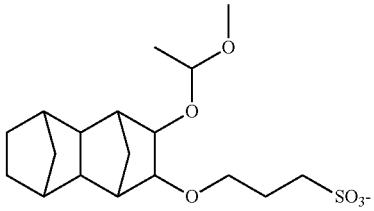
(A015) 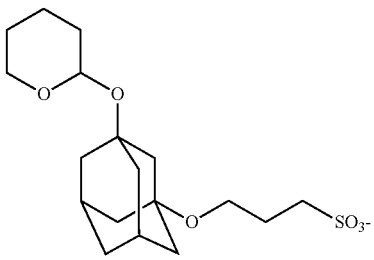
(A016) 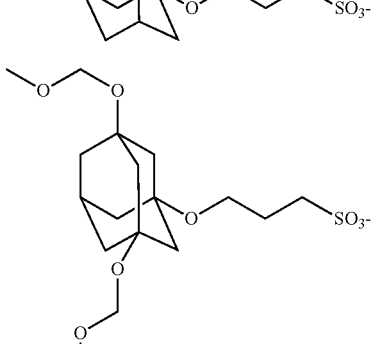
(A017) 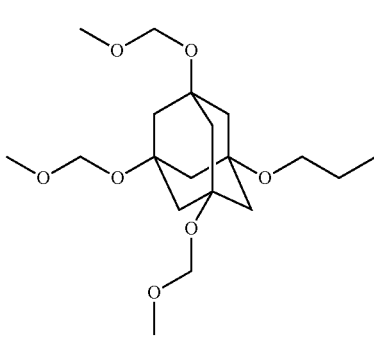
(A018) 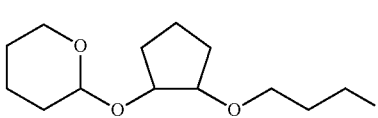
<<Cationic Moiety>>
In General Formula (X), $M^+$ represents a monovalent cation.
The monovalent cation is not particularly limited, but suitable examples thereof include a compound represented by General Formula (ZI) or General Formula (ZII).

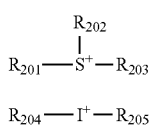
(ZI)

(ZII)

In General Formula (ZI), $R_{201}$, $R_{202}$, and $R_{203}$ each independently represent an organic group.

The number of carbon atoms in the organic group as each of $R_{201}$, $R_{202}$, and $R_{203}$ is generally 1 to 30, and preferably 1 to 20.

In addition, two of $R_{201}$ to $R_{203}$ may be bonded to each other to form a ring structure, and the ring may include an oxygen atom, a sulfur atom, an ester bond, an amide bond, or a carbonyl group. Examples of the group formed by the bonding of two of $R_{201}$ to $R_{203}$ include an alkylene group (for example, a butylene group and a pentylene group).

Examples of the organic group of each of $R_{201}$, $R_{202}$, and $R_{203}$ include an aryl group, an alkyl group, and a cycloalkyl group.

It is preferable that at least one of $R_{201}$, $R_{202}$, or $R_{203}$ is an aryl group, and it is more preferable that all of $R_{201}$, $R_{202}$, and $R_{203}$ represent an aryl group. As the aryl group, not only a phenyl group, a naphthyl group, or the like but also a heteroaryl group such as an indole residue and a pyrrole residue can also be used.

As the alkyl group of each of $R_{201}$ to $R_{203}$, a linear or branched alkyl group having 1 to 10 carbon atoms is preferable, and a methyl group, an ethyl group, an n-propyl group, an i-propyl group, or an n-butyl group is more preferable.

As the cycloalkyl group of each of $R_{201}$ to $R_{203}$, a cycloalkyl group having 3 to 10 carbon atoms is preferable, and a cyclopropyl group, a cyclobutyl group, a cyclopentyl group, a cyclohexyl group, or a cycloheptyl group is more preferable.

Examples of the substituent which may be contained in these groups include a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), and an alkoxycarbonyloxy group (preferably having 2 to 7 carbon atoms).

The alkyl group, the cycloalkyl group, and the aryl group exemplified above may have a substituent. The substituent is not particularly limited, but specific examples of the substituent include a nitro group, a halogen atom such as fluorine atom, a carboxyl group, a hydroxyl group, an amino group, a cyano group, an alkoxy group (preferably having 1 to 15 carbon atoms), an alkyl group (preferably having 1 to 10 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 1 to 15 carbon atoms), and an aryloxysulfonyl group (preferably having 6 to 20 carbon atoms).

In General Formula (ZII), $R_{204}$ and $R_{205}$ each independently represent an aryl group, an alkyl group, or a cycloalkyl group.

As the aryl group, the alkyl group, and the cycloalkyl group of each of $R_{204}$ and $R_{205}$ have the same definitions as the aryl group, the alkyl group, and the cycloalkyl group, respectively, of each of $R_{201}$ to $R_{203}$ in General Formula (ZI) as described above.

The substituent which may be contained in each of the aryl group, the alkyl group, and the cycloalkyl group of each of $R_{204}$ to $R_{205}$ is the same as the substituent which may be contained in each of the aryl group, the alkyl group, and the cycloalkyl group of each of $R_{201}$ to $R_{203}$ in the compound (ZI) as described above, and suitable aspects are also the same.

As the monovalent cation represented by M⁺ in General Formula (X), the cation represented by General Formula (ZI) as described above is preferable, and a substituted or unsubstituted triphenylsulfonium cation is more preferable.

<<Specific Examples of Cationic Moiety>>

Specific examples of the cationic moiety of the photoacid generator represented by General Formula (X) are shown below. It should be noted that the present invention is not particularly limited to specific examples shown below.

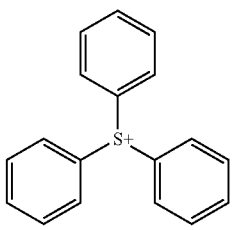
(C001)

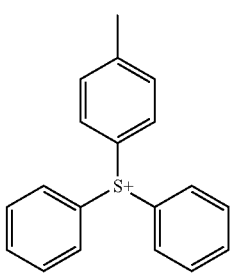
(C002)

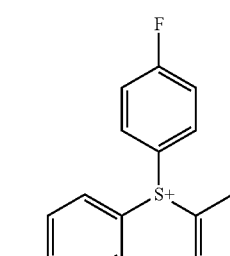
(C003)

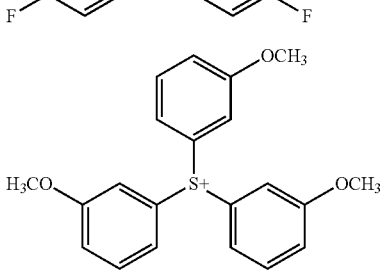
(C004)

(C005)
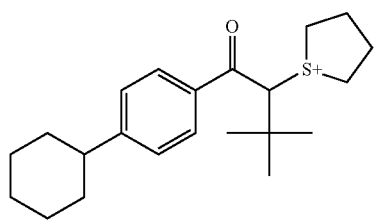
(C006)
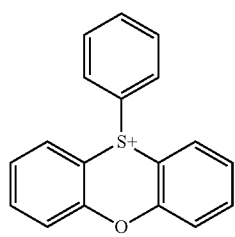
(C007)
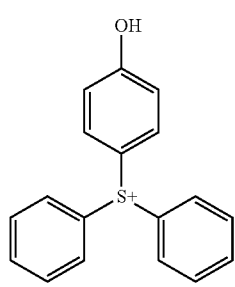
(C008)
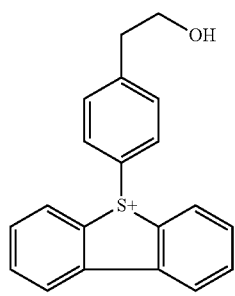
(C009)
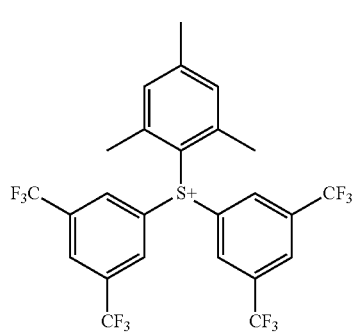
(C010)
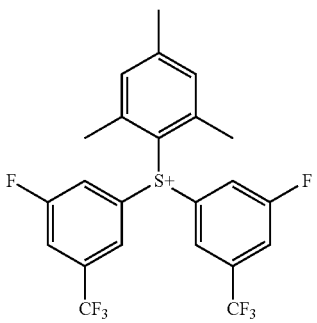
(C011)
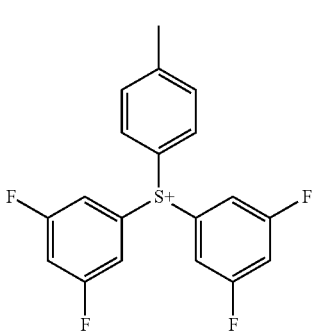
(C012)
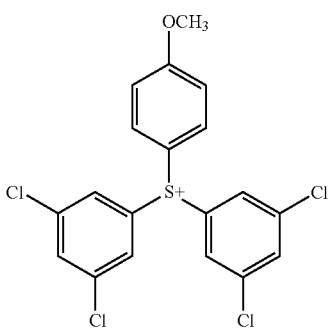
(C013)
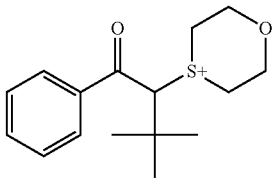
(C014)
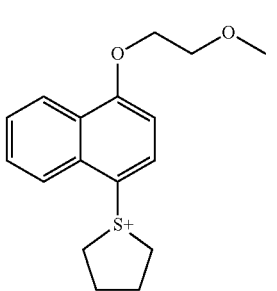

-continued (C015)

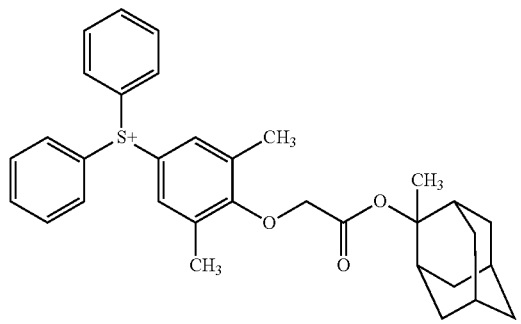

*<<Method for Synthesizing Compound Represented by General Formula (X)>>*

The compound represented by General Formula (X) (photoacid generator) can be synthesized by, for example, appropriately combining the following methods (a) to (c).

(a) Method for Introducing $A^{101}$ $A^{101}$ in General Formula (X) can be introduced by, for example, the following scheme. As a precursor of the $A^{101}$ moiety, a corresponding ketone compound, aldehyde compound, vinyl ether compound, a geminal haloalkoxymethyl compound, or the like can be used.

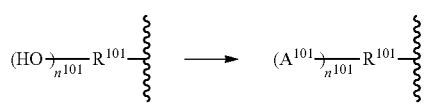

(b) Method for Introducing Sulfonic Acid Group

A method for introducing the sulfonic acid group in General Formula (X) is not particularly limited, but the positions of $L^{101}$ to sulfonic acid group moieties (group moieties) can be constructed by, for example, a reaction of a cyclic sultone compound such as propane sultone and butane sultone with an alkoxy compound or a carboxyl compound.

(c) Synthesis of Photoacid Generator

The photoacid generator represented by General Formula (X) can be synthesized by a salt exchange between a corresponding anion and a corresponding cation.

Specifically, the photoacid generator can be synthesized by, for example, thoroughly mixing a salt of a corresponding anion (for example, a metal salt and a quaternary ammonium salt) and an equimolar amount of a halide of a corresponding cation, and the like with a water-organic solvent (chloroform, methylene chloride, or the like), combining the organic solvent layer, and further washing the layer with water, followed by performing concentration.

<<Content and The Like>>

The photoacid generator may be used singly or in combination of two or more kinds thereof.

The content of the photoacid generator (a total content in a case where a plurality of the photoacid generators are present) in the composition of the embodiment of the present invention is preferably 0.1% to 50% by mass, more preferably 5% to 40% by mass, and still more preferably 5% to 35% by mass, with respect to a total solid content of the composition.

<Resin>

The composition of the embodiment of the present invention contains a resin whose polarity increases by the action of an acid (hereinafter also referred to as a "resin (X)").

Therefore, in the pattern forming method of an embodiment of the present invention which will be described later, typically, in a case where an alkali developer is adopted as the developer, a positive-tone pattern is suitably formed, and in a case where an organic developer is adopted as the developer, a negative-tone pattern is suitably formed.

<<Repeating Unit Represented by General Formula (B-1)>>

The resin (X) may include a repeating unit represented by General Formula (B-1) which will be described later. Hereinafter, the repeating unit represented by General Formula (B-1) included in the resin (X) will be described.

Furthermore, the resin (X) may include at least one halogen atom (hereinafter also referred to as a "specific halogen atom") selected from the group consisting of a fluorine atom and an iodine atom.

A position in the resin (X) to which the specific halogen atom is introduced is not particularly limited, but above all, the specific halogen atom is preferably included in the repeating unit represented by General Formula (B-1).

The content of the specific halogen atom in the resin (X) is not particularly limited, but is preferably 2% by mass or more with respect to a total mass of the resin. Further, an upper limit thereof is not particularly limited, but is, for example, 70% by mass.

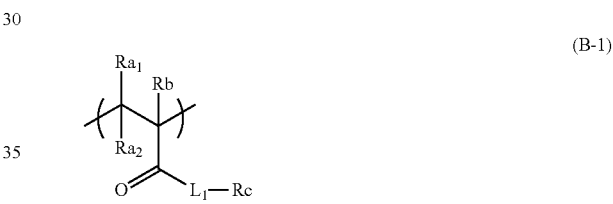

(B-1)

In General Formula (B-1), $Ra_1$ and $Ra_2$ each independently represent a hydrogen atom, an alkyl group, or an aryl group. It should be noted that one of $Ra_1$ and $Ra_2$ represents a hydrogen atom, and the other represents an alkyl group or an aryl group. Rb represents a hydrogen atom or a monovalent organic group. $L_1$ represents a divalent linking group selected from the group consisting of —O— and —N($R_A$)—. $R_A$ represents a hydrogen atom or a monovalent organic group. Rc represents a monovalent organic group.

The alkyl group represented by each of $Ra_1$ and $Ra_2$ is not particularly limited, but from the viewpoint that a pattern having a higher sensitivity and being excellent in LER and an ability to suppress collapse can be formed, an alkyl group having 1 to 8 carbon atoms (which may be any of linear, branched, and cyclic forms) is preferable, and examples thereof include a methyl group, an ethyl group, a propyl group, an n-butyl group, a sec-butyl group, a hexyl group, and an octyl group. Among those, a linear or branched alkyl group having carbon atoms 1 to 4 is more preferable.

The aryl group represented by each of $Ra_1$ and $Ra_2$ is not particularly limited, but from the viewpoint that a pattern having a higher sensitivity and being excellent in LER and an ability to suppress collapse can be formed, an aryl group having 6 to 10 carbon atoms is preferable. Examples of the aryl group include a phenyl group, a naphthyl group, and an anthryl group, and the phenyl group is preferable.

It should be noted that in General Formula (B-1), one of $Ra_1$ and $Ra_2$ represents a hydrogen atom, and the other represents an alkyl group or an aryl group. From the viewpoint that a pattern having a higher sensitivity and being excellent in LER and an ability to suppress collapse can be formed, it is preferable that one of $Ra_1$ and $Ra_2$ represents a hydrogen atom, and the other represents an aryl group.

$Ra_1$ and $Ra_2$ may further have a substituent.

The substituent contained in each of $Ra_1$ and $Ra_2$ is not particularly limited, and examples thereof include the groups exemplified in the above-described substituent group T, and more specifically include a halogen atom (a fluorine atom, a chlorine atom, a bromine atom, and an iodine atom), a cyano group, an alkyl group having 1 to 10 carbon atoms (for example, a methyl group, an ethyl group, and a propyl group), an alkoxy group having 1 to 10 carbon atoms (for example, a methoxy group and an ethoxy group), an acyl group having 1 to 10 carbon atoms (for example, a formyl group and an acetyl group), an alkoxycarbonyl group having 1 to 10 carbon atoms (for example, a methoxycarbonyl group and an ethoxycarbonyl group), an acyloxy group having 1 to 10 carbon atoms (for example, an acetyloxy group and a propionyloxy group), a nitro group, an alkyl group substituted with at least one fluorine atom (the alkyl group substituted with at least one fluorine atom is intended to mean an alkyl group in which a hydrogen atom is substituted with at least one fluorine atom; the number of carbon atoms of the alkyl group is preferably 1 to 10, and more preferably 1 to 6; and at least one or more fluorine atoms only need to be substituted, but a perfluoroalkyl group is preferable), and an acid group (a hydroxyl group, a carboxyl group, a hexafluoroisopropanol group, and a sulfonic acid group).

Among those, the fluorine atom, the iodine atom, the alkyl group substituted with at least one fluorine atom, or the acid group is preferable, and the fluorine atom, the iodine atom, the perfluoroalkyl group having 1 to 6 carbon atoms, or the acid group is more preferable.

The monovalent organic group represented by Rb is not particularly limited, and examples thereof include the groups exemplified as the above-described substituent group T, and more specifically include an alkyl group, an aryl group, a halogen atom (a fluorine atom, a chlorine atom, a bromine atom, and an iodine atom), and a hydroxyl group.

The alkyl group and the aryl group represented by Rb have the same definitions as the alkyl group and the aryl group represented by $Ra_1$, respectively, and suitable aspects thereof are also the same.

Among those, the hydrogen atom is preferable as Rb.

$L_1$ represents a divalent linking group selected from the group consisting of —O— and —N($R_A$)—.

$R_A$ represents a hydrogen atom or a monovalent organic group. The monovalent organic group represented by $R_A$ is not particularly limited, and examples thereof include an alkyl group having 1 to 10 carbon atoms, which may have a substituent (for example, the groups exemplified as the above-described substituent group T), with an alkyl group having 1 to 6 carbon atoms, which may have a substituent (for example, the groups exemplified as the above-described substituent group T) being preferable. Examples of $R_A$ include a methyl group, an ethyl group, a propyl group, an n-butyl group, a sec-butyl group, a hexyl group, and an octyl group.

Among those, the hydrogen atom is preferable as $R_A$.

The monovalent organic group represented by Rc is not particularly limited, and examples thereof include the groups exemplified as the above-described substituent group T, and more specifically include a halogen atom (a fluorine atom, a chlorine atom, a bromine atom, and an iodine atom), an alkyl group, an alkyl group substituted with at least one fluorine atom, an aralkyl group, a group that leaves through decomposition by the action of an acid (hereinafter also referred to as a "leaving group"), and a group including a lactone structure.

The alkyl group is not particularly limited, but is preferably an alkyl group having 1 to 8 carbon atoms, which may have a substituent (for example, the groups exemplified as the above-described substituent group T), and examples of the alkyl group include a methyl group, an ethyl group, a propyl group, an n-butyl group, a sec-butyl group, a hexyl group, and an octyl group. Among those, a linear or branched alkyl group having 1 to 4 carbon atoms is more preferable.

The alkyl group substituted with at least one fluorine atom is intended to mean an alkyl group in which a hydrogen atom is substituted with at least one fluorine atom. The number of carbon atoms of the alkyl group is preferably 1 to 10, more preferably 1 to 6, and still more preferably 1 to 3. In addition, a perfluoroalkyl group is preferable as the alkyl group substituted with at least one fluorine atom.

The aralkyl group is not particularly limited, but for example, the number of carbon atoms of the alkyl group in the aralkyl group is preferably 1 to 6, and more preferably 1 to 3. Examples of the aralkyl group include a benzyl group and a phenethyl group.

Examples of the leaving group include —C($R_{36}$)($R_{37}$)($R_{38}$), —C($R_{36}$)($R_{37}$)($OR_{39}$), and —C($R_{01}$)($R_{02}$)($OR_{39}$).

In the formulae, $R_{36}$ to $R_{39}$ each independently an alkyl group, a cycloalkyl group, an aryl group, an aralkyl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, an aralkyl group, or an alkenyl group.

As the alkyl group as each of $R_{36}$ to $R_{39}$, $R_{01}$, and $R_{02}$, an alkyl group having 1 to 8 carbon atoms is preferable, and examples thereof include a methyl group, an ethyl group, a propyl group, an n-butyl group, a sec-butyl group, a hexyl group, and an octyl group.

The cycloalkyl group as each of $R_{36}$ to $R_{39}$, $R_{01}$, and $R_{02}$ may be either a monocycle or polycycle. As the monocyclic cycloalkyl group, a cycloalkyl group having 3 to 8 carbon atoms is preferable, and examples thereof include a cyclopropyl group, a cyclobutyl group, a cyclopentyl group, a cyclohexyl group, and a cyclooctyl group. As the polycyclic cycloalkyl group, a cycloalkyl group having 6 to 20 carbon atoms is preferable, and examples thereof include an adamantyl group, a norbornyl group, an isobornyl group, a camphanyl group, a dicyclopentyl group, an α-pinel group, a tricyclodecanyl group, a tetracyclododecyl group, and an androstanyl group. Further, at least one carbon atom in the cycloalkyl group may be substituted with a heteroatom such as an oxygen atom.

The aryl group as each of $R_{36}$ to $R_{39}$, $R_{01}$, and $R_{02}$ is preferably an aryl group having 6 to 10 carbon atoms, and examples thereof include a phenyl group, a naphthyl group, and an anthryl group.

The aralkyl group as each of $R_{36}$ to $R_{39}$, $R_{01}$, and $R_{02}$ is preferably an aralkyl group having 7 to 12 carbon atoms, and examples thereof include a benzyl group, a phenethyl group, and a naphthylmethyl group.

The alkenyl group as each of $R_{36}$ to $R_{39}$, $R_{01}$, and $R_{02}$ is preferably an alkenyl group having 2 to 8 carbon atoms, and examples thereof include a vinyl group, an allyl group, a butenyl group, and a cyclohexenyl group.

The ring formed by the bonding of $R_{36}$ and $R_{37}$ is preferably a (monocyclic or polycyclic) cycloalkyl group. As the cycloalkyl group, a monocyclic cycloalkyl group such as a cyclopentyl group and a cyclohexyl group, and a polycyclic cycloalkyl group such as a norbornyl group, a tetracyclodecanyl group, a tetracyclododecanyl group, and an adamantyl group are preferable.

The above-described aralkyl group and leaving group may each have a substituent. The substituent is not particularly limited, but for example, substituents exemplified as the substituent of each of $Ra_1$ and $Ra_2$ are preferable, among which the fluorine atom, the iodine atom, or the alkyl group substituted with at least one fluorine atom is more preferable, and the fluorine atom, the iodine atom, or the perfluoroalkyl group having 1 to 6 carbon atoms is still more preferable.

The group including a lactone structure is not particularly limited as long as it includes a lactone structure.

As the lactone structure, a 5- to 7-membered ring lactone structure is preferable, and a 5- to 7-membered ring lactone structure to which another ring structure is fused so as to form a bicyclo structure or spiro structure is more preferable.

As the lactone structure, lactone structures represented by General Formulae (LC1-1) to (LC1-17) are preferable, and among these, the group represented by General Formula (LC1-1), General Formula (LC1-4), General Formula (LC1-5), General Formula (LC1-6), General Formula (LC1-13), or General Formula (LC1-14) is more preferable. A lactone structure from which any one of hydrogen atoms is removed is derived into a group including the lactone structure.

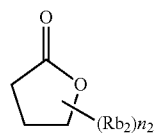

LC1-1

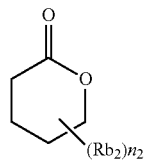

LC1-2

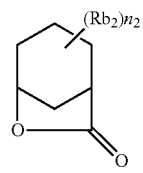

LC1-3

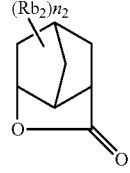

LC1-4

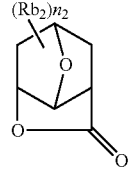

LC1-5

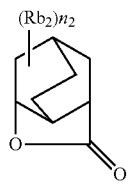

LC1-6

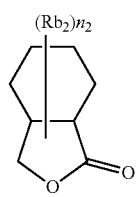

LC1-7

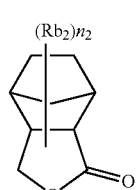

LC1-8

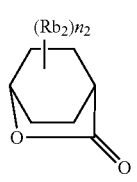

LC1-9

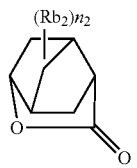

LC1-10

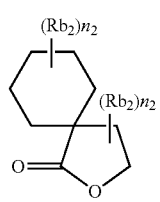

LC1-11

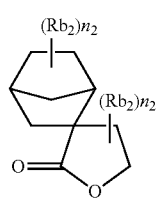

LC1-12

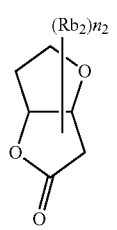

LC1-13

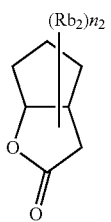
LC1-14

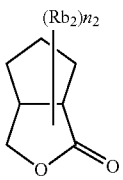
LC1-15

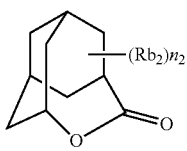
LC1-16

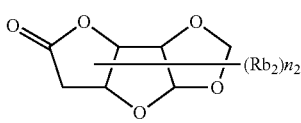
LC1-17

The lactone structural moiety may have a substituent ($Rb_2$). Examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, and an acid-decomposable group, and an alkyl group having 1 to 4 carbon atoms, a cyano group, or an acid-decomposable group is preferable. $n_2$ represents an integer of 0 to 4. In a case % here $n_2$ is 2 or more, a plurality of the substituents ($Rb_2$) may be the same as or different from each other. Further, a plurality of the substituents ($Rb_2$) may be bonded to each other to form a ring.

In a case where Rc includes the lactone structure, it is preferable that Rc is represented by General Formula (A1).

-$L_2$-$Rc_1$　　　　　　　　　　　　　General Formula (A1):

In General Formula (A1), $L_2$ represents a single bond or a divalent linking group, and $Rc_1$ represents a group formed by removing any one of hydrogen atoms from a lactone structure.

The divalent linking group is not particularly limited, but examples thereof include —CO—, —O—, —N($R_B$)—, an alkylene group (preferably having 1 to 6 carbon atoms), a cycloalkylene group (preferably having 3 to 15 carbon atoms), an alkenylene group (preferably having 2 to 6 carbon atoms), and a divalent linking group formed by combination of a plurality of these groups. $R_B$ represents a hydrogen atom or a monovalent organic group. The monovalent organic group represented by $R_B$ is not particularly limited, but represents, for example, an alkyl group having 1 to 10 carbon atoms.

The group formed by removing any one of hydrogen atoms from a lactone structure, represented by $Rc_1$, is the same as described above.

Among those, $L_2$ is preferably the single bond.

Among the repeating units represented by General Formula (B-1), from the viewpoint that a pattern having a higher sensitivity and being excellent in LER and an ability to suppress collapse can be formed, in particular, a repeating unit represented by General Formula (B-2) is preferable.

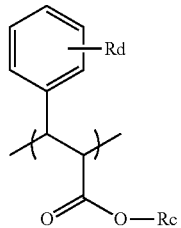
(B-2)

In General Formula (B-2), Rc represents a monovalent organic group. Rd represents a hydrogen atom or a monovalent organic group.

In General Formula (B-2), the monovalent organic group represented by Rc has the same definition as Rc in General Formula (B-1), and suitable aspects thereof are also the same. Examples of the monovalent organic group represented by Rd include the same ones the substituents of each of $Ra_1$ and $Ra_2$ as described above, and suitable aspects thereof are also the same.

Specific examples of the repeating unit represented by General Formula (B-1) are shown below, but the present invention is not limited to these specific examples.

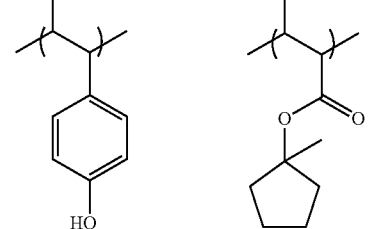

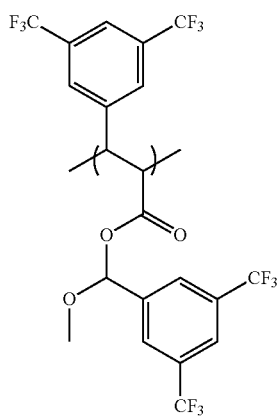
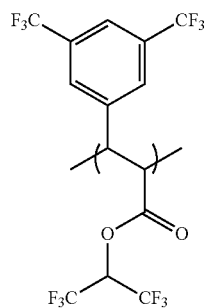

represented by General Formula (B-2), in which a content of a halogen atom selected from the group consisting of a fluorine atom and the halogen atom (hereinafter also referred to as a "content of a specific halogen atom") is 10% by mass or more, is preferable. From the viewpoint that a pattern having a higher sensitivity and being excellent in LER and an ability to suppress collapse can be formed, the content of the specific halogen atom is more preferably 12% by mass or more, still more preferably 25% by mass or more, and particularly preferably 30% by mass or more. In addition, an upper limit value thereof is not particularly limited, but is, for example, 80% by mass or less.

The repeating unit represented by General Formula (B-2) is preferably at least one repeating unit selected from the group consisting of the following repeating unit (A), the following repeating unit (B), and the following repeating unit (C).

Repeating unit (A): Repeating unit represented by General Formula (B-2), in which Rc represents a group including a lactone structure.

Repeating unit (B): Repeating unit represented by General Formula (B-2), in which Rc represents a group that leaves through decomposition by the action of an acid (leaving group).

Repeating unit (C): Repeating unit represented by General Formula (B-2), in which Rd represents an acid group.

Furthermore, the group including a lactone structure represented by Rc, the leaving group represented by Rc, and the acid group represented by Rd are each the same as described above.

Among those, from the viewpoint that a pattern having a higher sensitivity and being excellent in LER and an ability to suppress collapse can be formed, the content of the specific halogen atom in any of the repeating unit (A), the repeating unit (B), and the repeating unit (C) is preferably 10% by mass or more, more preferably 12% by mass or more, still more preferably 25% by mass or more, and particularly preferably 30% by mass or more, and is also preferably 80% by mass or less. In addition, in a case where a specific halogen atom is introduced into the repeating unit (B), from the viewpoint that a pattern having a higher sensitivity and being excellent in LER and an ability to suppress collapse can be formed, it is preferable that the specific halogen atom is introduced into a position other than the leaving group.

Among those, from the viewpoint that a pattern having a higher sensitivity and being excellent in LER and an ability to suppress collapse can be formed, the resin (X) preferably includes at least two or more repeating units selected from the group consisting of the repeating unit (A), the repeating unit (B), and the repeating unit (C), and more preferably includes all of the repeating unit (A), the repeating unit (B), and the repeating unit (C).

The resin (X) may further include other repeating units, in addition to the repeating unit represented by General Formula (B-1). In addition, the content of the repeating unit represented by General Formula (B-1) in the resin (X) is not particularly limited, but is, for example, 5% to 100% by mass with respect to all the repeating units in the resin (X).

Hereinafter, such other repeating units which can be included in the resin (X) will be described in detail. The resin (X) may include a repeating unit which will be described later while not including the repeating unit represented by General Formula (B-1).

In a case where the resin (X) includes such other repeating units, the content of the repeating unit represented by General Formula (B-1) is preferably 5% to 80% by mass, more preferably 5% to 70% by mass, and still more preferably 10% to 60% by mass, with respect to all the repeating units in the resin (X).

In the resin (X), the total amount of the repeating unit (corresponding to, for example, the above-described repeating unit (B) and a repeating unit Y1 which will be described later) including the acid-decomposable group is preferably 10% by mass or more, and more preferably 15% by mass or more, and is also preferably 50% by mass or less, and more preferably 40% by mass or less, with respect to all the repeating units in the resin (X).

In the resin (X), the total amount of the repeating units (corresponding to, for example, the above-described repeating unit (C), a repeating unit Y3 which will be described later, and a repeating unit Y4 which will be described later) including an acid group is preferably 20% by mass or more, and more preferably 30% by mass or more, and is also preferably 80% by mass or less, and more preferably 70% by mass or less, with respect to all the repeating units in the resin (X).

<<Repeating Unit Having Acid-Decomposable Group>>

The resin (X) may further include another repeating unit having an acid-decomposable group (hereinafter also referred to as a "repeating unit Y1"), in addition to the repeating unit represented by General Formula (B-1).

The acid-decomposable group preferably has a structure in which a polar group is protected with a group that leaves through decomposition by the action of an acid (leaving group).

Examples of the polar group include an acidic group (a group which dissociates in a 2.38%-by-mass aqueous tetramethylammonium hydroxide solution), such as a carboxyl group, a phenolic hydroxyl group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group, and an alcoholic hydroxyl group.

Moreover, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol (for example, a hexafluoroisopropanol group) having the α-position substituted with an electron withdrawing group such as a fluorine atom is excluded as a hydroxyl group. The alcoholic hydroxyl group is preferably a hydroxyl group having an acid dissociation constant (pKa) from 12 to 20.

Preferred examples of the polar group include a carboxyl group, a phenolic hydroxyl group, a fluorinated alcohol group (preferably a hexafluoroisopropanol group), and a sulfonic acid group, and among these, a phenolic hydroxyl group is preferable.

The group which is preferable as the acid-decomposable group is a group in which a hydrogen atom is substituted with a group that leaves by the action of an acid (leaving group). The leaving group has the same definition as the leaving group represented by Rc and suitable aspects thereof are also the same.

As the leaving group, among the leaving groups represented by Rc, the above-described formula —C($R_{01}$)($R_{02}$)(O$R_{39}$) is more preferable.

As the repeating unit Y1, a repeating unit represented by General Formula (AI) is preferable.

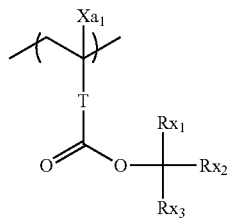

(AI)

In General Formula (AI), $Xa_1$ represents a hydrogen atom, a halogen atom, or an alkyl group which may have a substituent.

T represents a single bond or a divalent linking group.

$Rx_1$ to $Rx_3$ each independently represent an (linear or branched) alkyl group or a (monocyclic or polycyclic) cycloalkyl group. It should be noted that in a case where all of $Rx_1$ to $Rx_3$ are (linear or branched) alkyl groups, it is preferable that at least two of $Rx_1$, ..., or $Rx_3$ are methyl groups.

Two of $Rx_1$ to $Rx_3$ may be bonded to each other to form a (monocyclic or polycyclic) cycloalkyl group.

Examples of the alkyl group which may have a substituent, represented by $Xa_1$, include a methyl group or a group represented by —$CH_2$—$R_{11}$. $R_{11}$ represents a halogen atom (a fluorine atom and the like), a hydroxyl group, or a monovalent organic group, for example, an alkyl group having 5 or less carbon atoms and an acyl group having 5 or less carbon atoms; the alkyl group having 3 or less carbon atoms is preferable; and the methyl group is more preferable.

Examples of the halogen atom represented by $Xa_1$ include a fluorine atom, a chlorine atom, a bromine atom, and an iodine atom, and the fluorine atom or the iodine atom is preferable.

As $Xa_1$, a hydrogen atom, a fluorine atom, an iodine atom, a methyl group, a trifluoromethyl group, or a hydroxymethyl group is preferable.

Examples of the divalent linking group represented by T include an alkylene group, an arylene group, a —COO-Rt-group, and an —O-Rt-group. In the formulae. Rt represents an alkylene group or a cycloalkylene group.

T is preferably a single bond or a —COO-Rt-group. In a case where T represents a —COO-Rt-group, Rt is preferably an alkylene group having 1 to 5 carbon atoms, and more preferably a —$CH_2$— group, a —$(CH_2)_2$— group, or a —$(CH_2)_3$— group.

As the alkyl group represented by each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group represented by each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of two of $Rx_1$ to $Rx_3$, a monocyclic cycloalkyl group such as a cyclopentyl group and a cyclohexyl group is preferable, and in addition, a polycyclic cycloalkyl group such as a norbornyl group, a tetracyclodecanyl group, a tetracyclododecanyl group, and an adamantyl group is also preferable. Among those, a monocyclic cycloalkyl group having 5 or 6 carbon atoms is preferable.

In the cycloalkyl group formed by the bonding of two of Rx$_1$ to Rx$_3$, for example, one of the methylene groups constituting the ring may be substituted with a heteroatom such as an oxygen atom, or a group having a heteroatom, such as a carbonyl group.

In a case where each of the groups has a substituent, examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). The number of carbon atoms in the substituent is preferably 8 or less.

Specific examples of the repeating unit Y1 are shown below, but the present invention is not particularly limited to these specific examples.

In the specific examples, Rx represents a hydrogen atom, a fluorine atom, an iodine atom, CH$_3$, CF$_3$, or CH$_2$OH. Rxa and Rxb each represent an alkyl group having 1 to 4 carbon atoms. Z represents a substituent including a polar group, and in a case where Z's are present in plural number, Z's are independent. p represents 0 or a positive integer. Examples of the substituent including a polar group represented by Z include a linear or branched alkyl group or alicyclic group, which has a hydroxyl group, a cyano group, an amino group, an alkylamido group, or a sulfonamido group, and an alkyl group having a hydroxyl group is preferable. As the branched alkyl group, an isopropyl group is preferable.

1

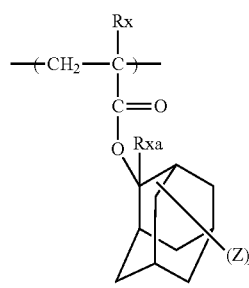

2

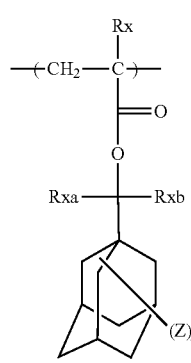

3

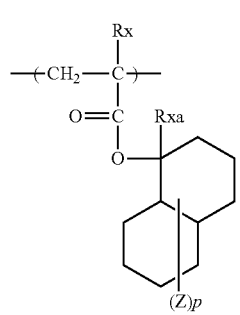

-continued

4

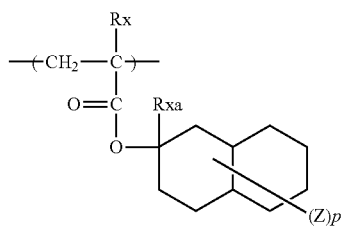

5

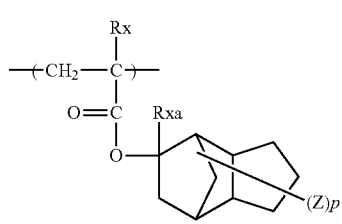

6

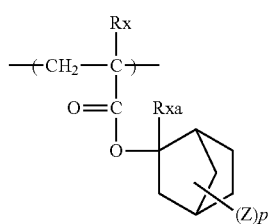

7

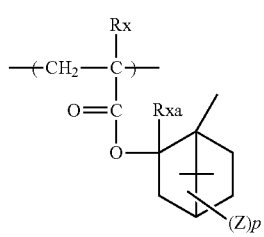

8

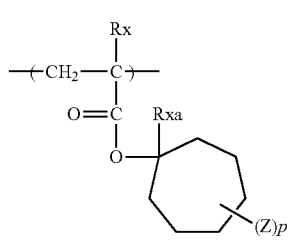

9

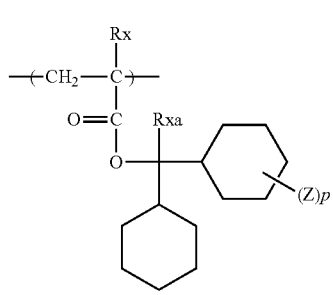

10

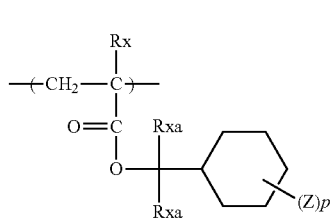

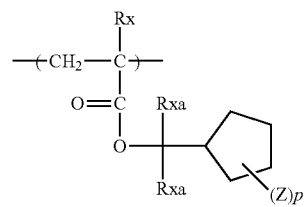
11
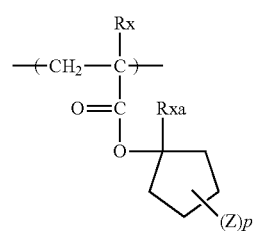
12
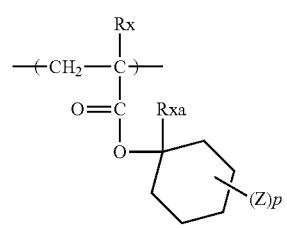
13
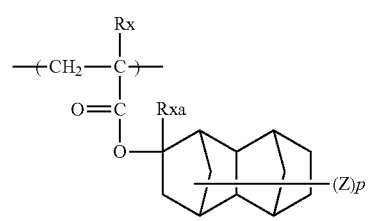
14
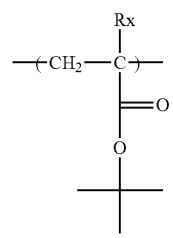
15
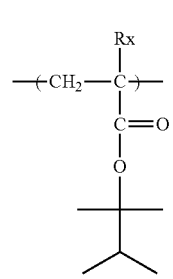
16
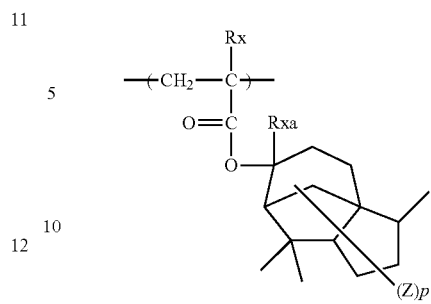
17
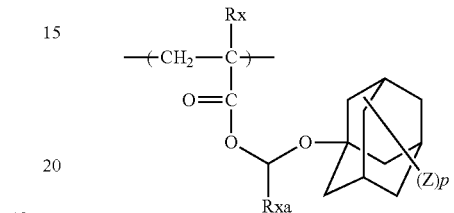
18
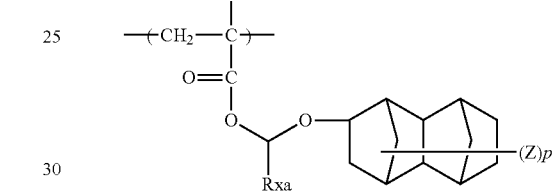
19
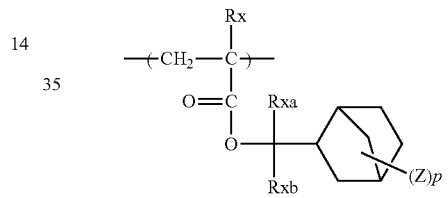
20
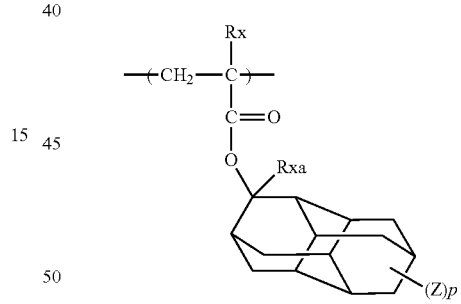
21
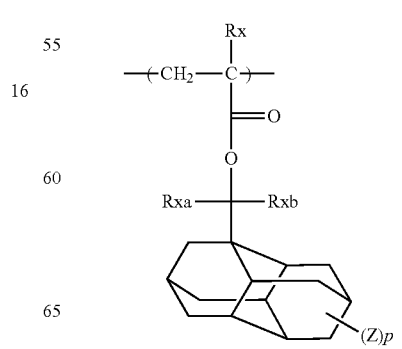
22

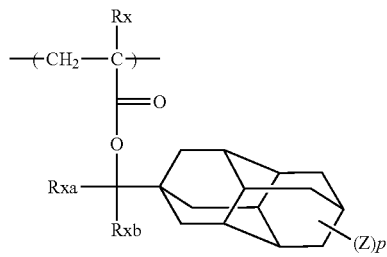

23

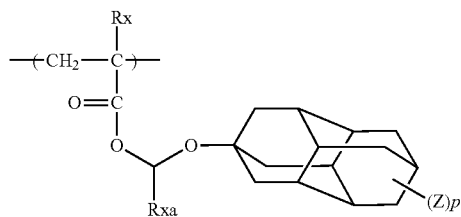

24

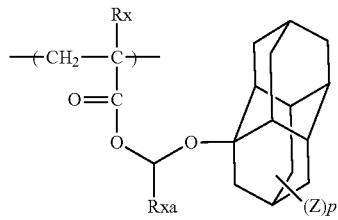

25

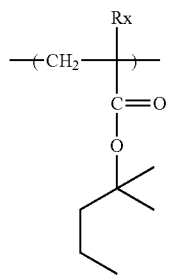

26

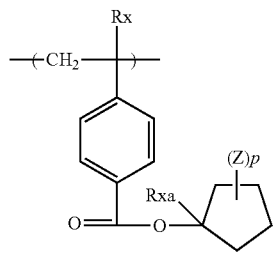

27

In a case where the resin (X) includes a repeating unit Y1, the content of the repeating unit Y1 is preferably 5% to 80% by mass, more preferably 5% to 70% by mass, and still more preferably 10% to 60% by mass, with respect to all the repeating units in the resin (X).

<<Other Repeating Unit Having Lactone Structure>>

The resin (X) may further include another repeating unit (hereinafter also referred to as a "repeating unit Y2") having a lactone structure, in addition to the repeating unit represented by General Formula (B-1).

Examples of repeating unit Y2 include a repeating unit represented by General Formula (AI).

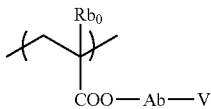

(AI)

In General Formula (AI), $Rb_0$ represents a hydrogen atom, a halogen atom, or an alkyl group having 1 to 4 carbon atoms.

The alkyl group of $Rb_0$ may have a substituent, and examples of the substituent include a hydroxyl group and a halogen atom (a fluorine atom, a chlorine atom, a bromine atom, and an iodine atom). Among those. $Rb_0$ is preferably a hydrogen atom or a methyl group.

In General Formula (AI), Ab represents a single bond, an alkylene group, a divalent linking group having a monocyclic or polycyclic alicyclic hydrocarbon structure, an ether group, an ester group, a carbonyl group, a carboxyl group, or a divalent group formed by combination thereof. Among those, the single bond or a linking group represented by -$Ab_1$-COO— is preferable. $Ab_1$ is a linear or branched alkylene group, or a monocyclic or polycyclic cycloalkylene group, and is preferably a methylene group, an ethylene group, a cyclohexylene group, an adamantylene group, or a norbornylene group.

V represents a group represented by any one of General Formula (LC1-1), . . . , or General Formula (LC1-17) which has the above-described lactone structure.

Optical isomers of the repeating unit Y2 are typically present, but any of the optical isomers may be used. In addition, one kind of optical isomers may be used singly or a mixture of a plurality of the optical isomers may be used. In a case where one kind of optical isomers are mainly used, the optical purity (ee) thereof is preferably 90 or more, and more preferably 95 or more.

Specific examples of the repeating unit Y2 are shown below, but the present invention is not particularly limited to these specific examples.

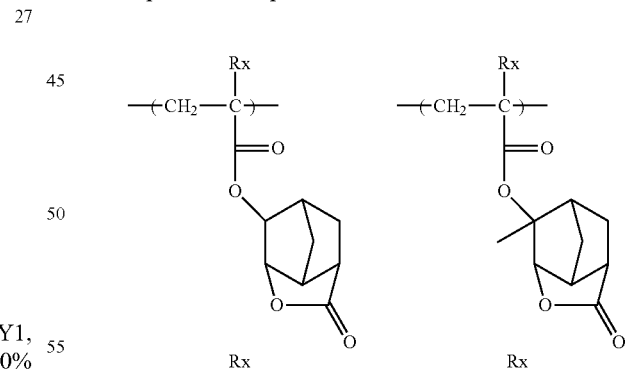

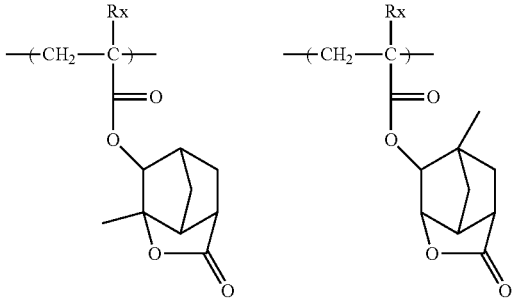

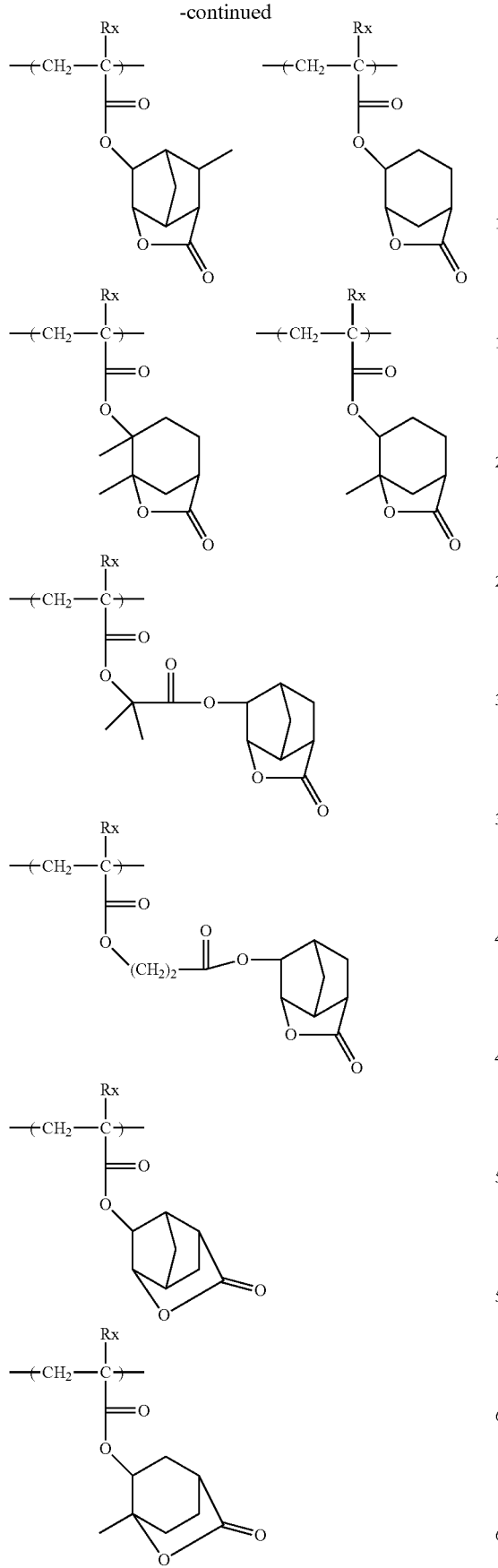
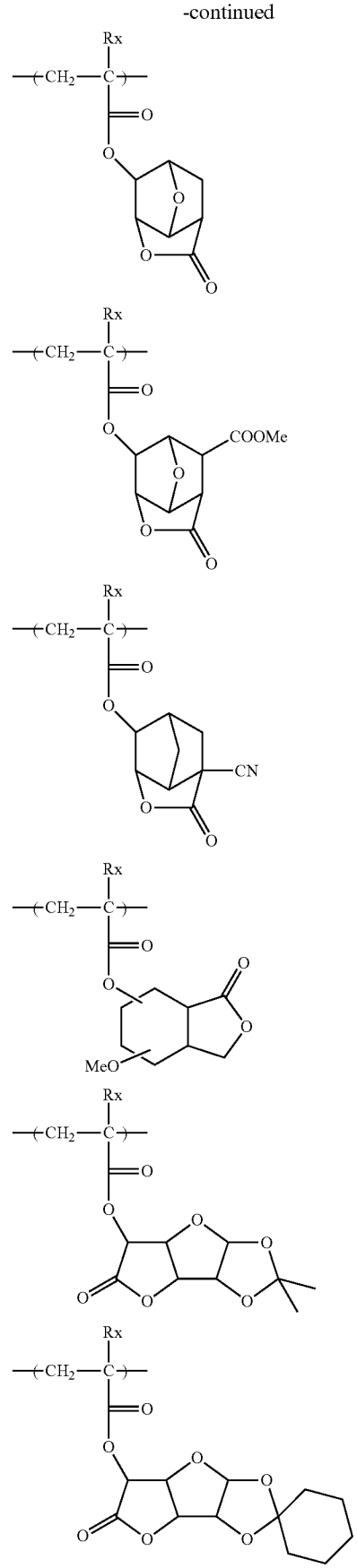

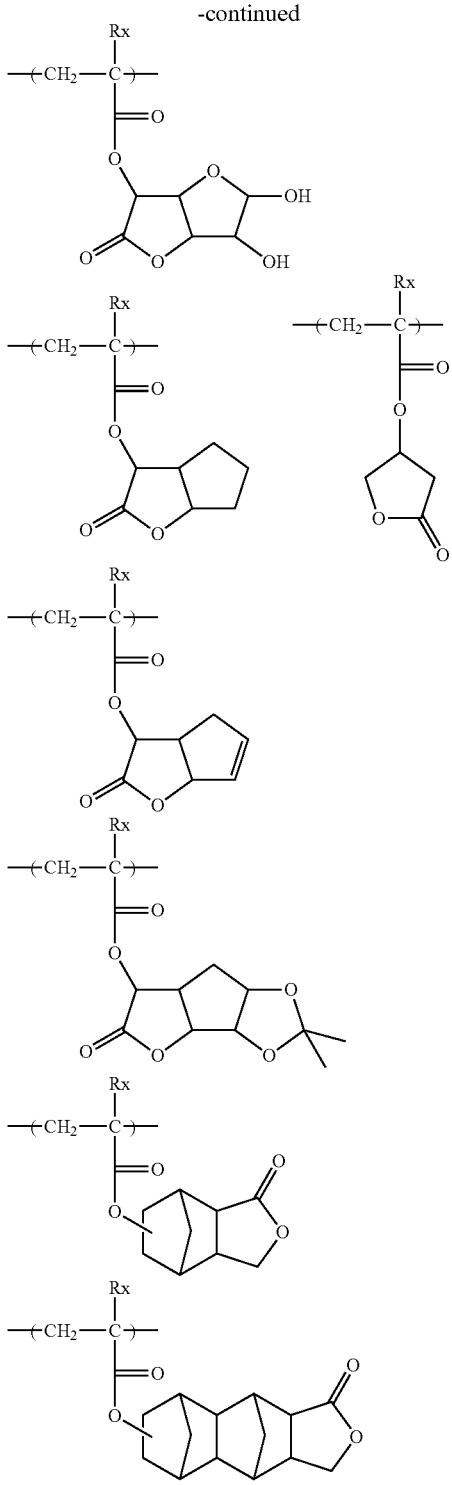

In a case where the resin (X) includes the repeating unit Y2, the content of the repeating unit Y2 is preferably 5% to 80% by mass, more preferably 5% to 70% by mass, and still more preferably 10% to 60% by mass, with respect to all the repeating units in the resin (X).

<<Repeating Unit Having Phenolic Hydroxyl Group>>

In a case where the resin (X) may further include another repeating unit having a phenolic hydroxyl group (hereinafter also referred to as a "repeating unit Y3"), in addition to the repeating unit represented by General Formula (B-1).

Examples of the repeating unit Y3 include a repeating unit represented by General Formula (I).

In the formula, $R_{41}$, $R_{42}$, and $R_{43}$ each independently represent a hydrogen atom, an alkyl group, a cycloalkyl group, a halogen atom, a cyano group, or an alkoxycarbonyl group. It should be noted that $R_{42}$ may be bonded to $Ar_4$ to form a ring, and in this case, $R_{42}$ represents a single bond or an alkylene group.

$X_4$ represents a single bond, —COO—, or —CONR$_{64}$—, and $R_{64}$ represents a hydrogen atom or an alkyl group.

$L_4$ represents a single bond or a divalent linking group.

$Ar_4$ represents an (n+1)-valent aromatic hydrocarbon group, and in a case where $Ar_4$ is bonded to $R_{42}$ to form a ring, $Ar_4$ represents an (n+2)-valent aromatic hydrocarbon group.

n represents an integer of 1 to 5.

For the purpose of increasing the polarity of the repeating unit represented by General Formula (I), it is preferable that n is an integer of 2 or more, or $X_4$ is —COO— or —CONR$_{64}$—.

As the alkyl group represented by each of $R_{41}$, $R_{42}$, and $R_{43}$ in General Formula (I), an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, each of which may have a substituent, is preferable, an alkyl group having 8 or less carbon atoms is more preferable, and an alkyl group having 3 or less carbon atoms is still more preferable.

The cycloalkyl group represented by each of $R_{41}$, $R_{42}$, and $R_{43}$ in General Formula (I) may be a monocycle or a polycycle. A monocyclic cycloalkyl group having 3 to 8 carbon atoms, such as a cyclopropyl group, a cyclopentyl group, and a cyclohexyl group, which may have a substituent, is preferable.

Examples of the halogen atom represented by each of $R_{41}$, $R_{42}$, and $R_{43}$ in General Formula (I) include a fluorine atom, a chlorine atom, a bromine atom and an iodine atom, and the fluorine atom is preferable.

As the alkyl group included in the alkoxycarbonyl group represented by each of $R_{41}$, $R_{42}$, and $R_{43}$ in General Formula (I), the same ones as the alkyl group in each of $R_{41}$, $R_{42}$, and $R_{43}$ are preferable.

Preferred examples of the substituent in each of the groups include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group, and the number of carbon atoms of the substituent is preferably 8 or less.

Ar$_4$ represents an (n+1)-valent aromatic hydrocarbon group. The divalent aromatic hydrocarbon group in a case where n is 1 may have a substituent, and for example, an arylene group having 6 to 18 carbon atoms, such as a phenylene group, a tolylene group, a naphthylene group, and an anthracenylene group, or an aromatic hydrocarbon group including a heterocycle such as thiophene, furan, pyrrole, benzothiophene, benzofuran, benzopyrrole, triazine, imidazole, benzimidazole, triazole, thiadiazole, and thiazole is preferable.

Specific suitable examples of the (n+1)-valent aromatic hydrocarbon group in a case where n is an integer of 2 or more include groups formed by excluding any (n−1) hydrogen atoms from the above-described specific examples of the divalent aromatic hydrocarbon group. The (n+1)-valent aromatic hydrocarbon group may further have a substituent.

Examples of the substituent which can be contained in the above-described alkyl group, cycloalkyl group, alkoxycarbonyl group, and (n+1)-valent aromatic hydrocarbon group include the alkyl groups mentioned in $R_{41}$, $R_{42}$, and $R_{43}$ in General Formula (I); an alkoxy group such as a methoxy group, an ethoxy group, a hydroxyethoxy group, a propoxy group, a hydroxypropoxy group, and a butoxy group; and an aryl group such as a phenyl group.

Preferred examples of the alkyl group of $R_{64}$ in —CONR$_{64}$— (R$_{64}$ represents a hydrogen atom or an alkyl group) represented by X$_4$ include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, each of which may have a substituent, and the alkyl group is more preferably an alkyl group having 8 or less carbon atoms.

As X$_4$, a single bond, —COO—, or —CONH— is preferable, and the single bond or —COO— is more preferable.

As the divalent linking group as L$_4$, an alkylene group is preferable, and as the alkylene group, an alkylene group having 1 to 8 carbon atoms, such as a methylene group, an ethylene group, a propylene group, a butylene group, a hexylene group, and an octylene group, each of which may have a substituent, is preferable.

As Ar$_4$, an aromatic hydrocarbon group having 6 to 18 carbon atoms, which may have a substituent, is preferable, and a benzene ring group, a naphthalene ring group, or a biphenylene ring group is more preferable. Among those, the repeating unit represented by General Formula (I) is preferably a repeating unit derived from hydroxystyrene. That is, Ar$_4$ is preferably a benzene ring group.

Specific examples of the repeating unit Y3 are shown below, but the present invention is not limited to these specific examples. In the formulae, a represents 1 or 2.

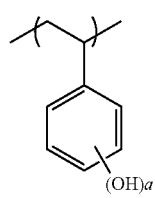
(B-1)

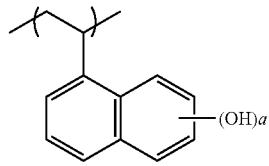
(B-2)

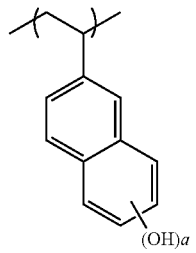
(B-3)

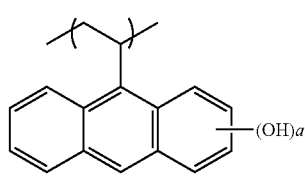
(B-4)

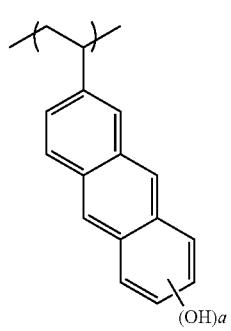
(B-5)

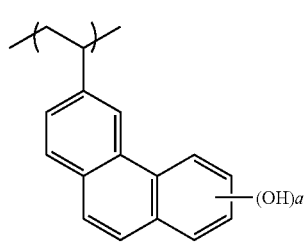
(B-6)

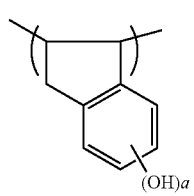
(B-7)

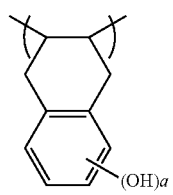
(B-8)

(B-9) 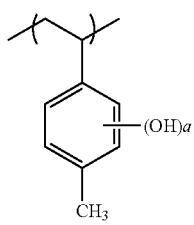
(B-10) 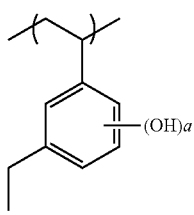
(B-11) 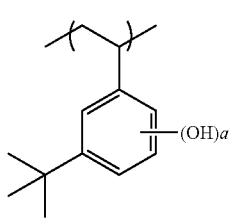
(B-12) 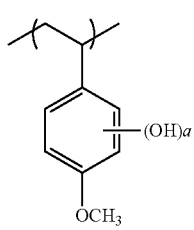
(B-13) 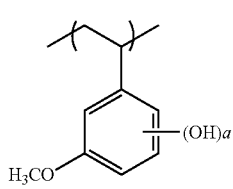
(B-14) 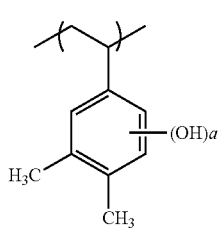
(B-15) 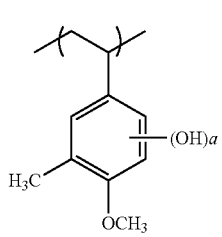
(B-16) 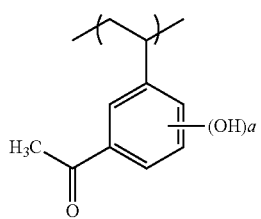
(B-17) 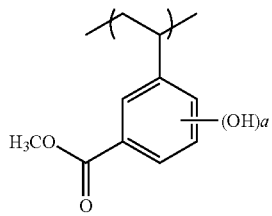
(B-18) 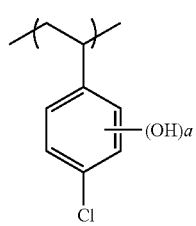
(B-19) 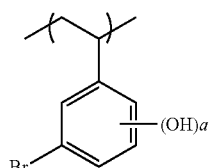
(B-20) 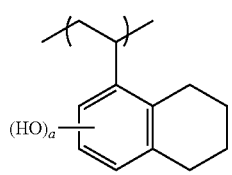
(B-21) 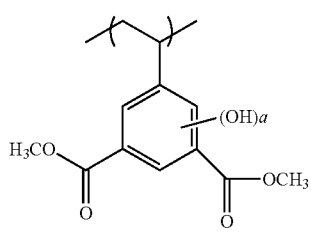
(B-22) 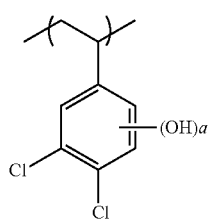

(B-23) 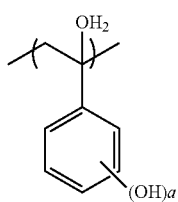

(B-24) 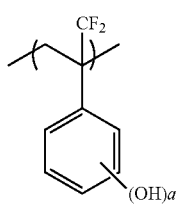

(B-25) 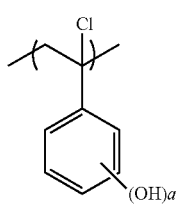

(B-26) 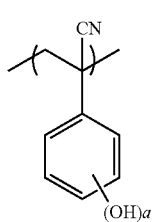

(B-27) 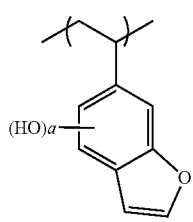

(B-28) 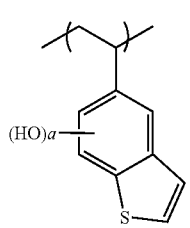

(B-29) 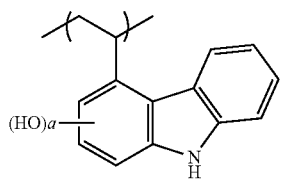

(B-30) 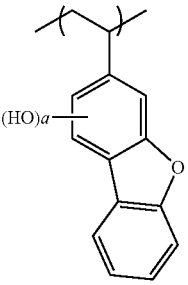

(B-31) 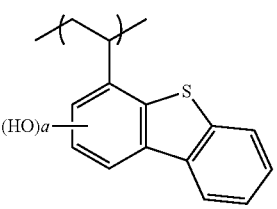

(B-32) 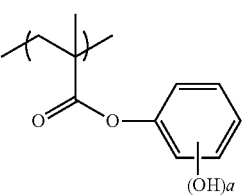

(B-33) 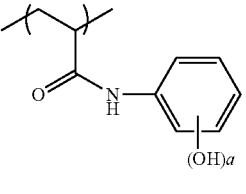

(B-34) 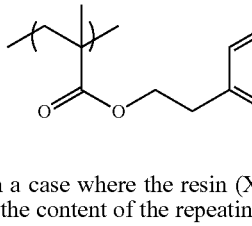

In a case where the resin (X) includes the repeating unit Y3, the content of the repeating unit Y3 is preferably 5% to 80% by mass, more preferably 5% to 70% by mass, and still more preferably 10% to 60% by mass, with respect to all the repeating units in the resin (A).

<<Other Repeating Unit Acid Group>>

The resin (X) may further include another repeating unit having an acid group (hereinafter also referred to as a "repeating unit Y4"), in addition to the repeating unit represented by General Formula (B-1) and the repeating unit Y3.

Examples of the acid group included in the repeating unit Y4 include a phenolic hydroxyl group, a carboxylic acid group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl) methylene group, a bis(alkylsulfonyl)imido group, a tris (alkylcarbonyl)methylene group, and a tris(alkylsulfonyl) methylene group.

As the acid group, the fluorinated alcohol group (preferably hexafluoroisopropanol), the sulfonimido group, or the bis(alkylcarbonyl)methylene group is preferable.

The skeleton of the repeating unit Y4 is not particularly limited, but the repeating unit Y4 is preferably a (meth)acrylate-based repeating unit or a styrene-based repeating unit.

Specific examples of the repeating unit Y4 are shown below, but the present invention is not limited to these specific examples. In the formulae, Rx represents a hydrogen atom, $CH_3$, $CF_3$, or $CH_2OH$.

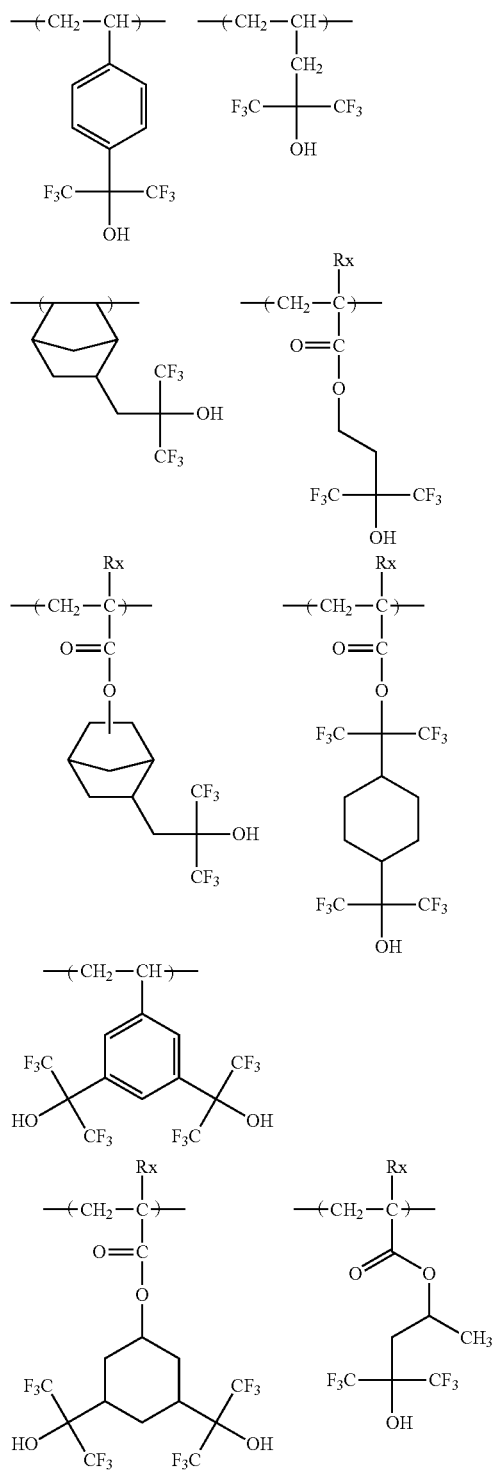

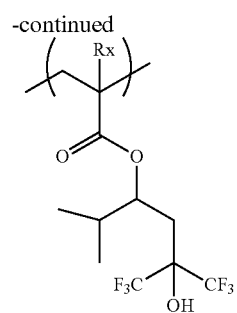

-continued

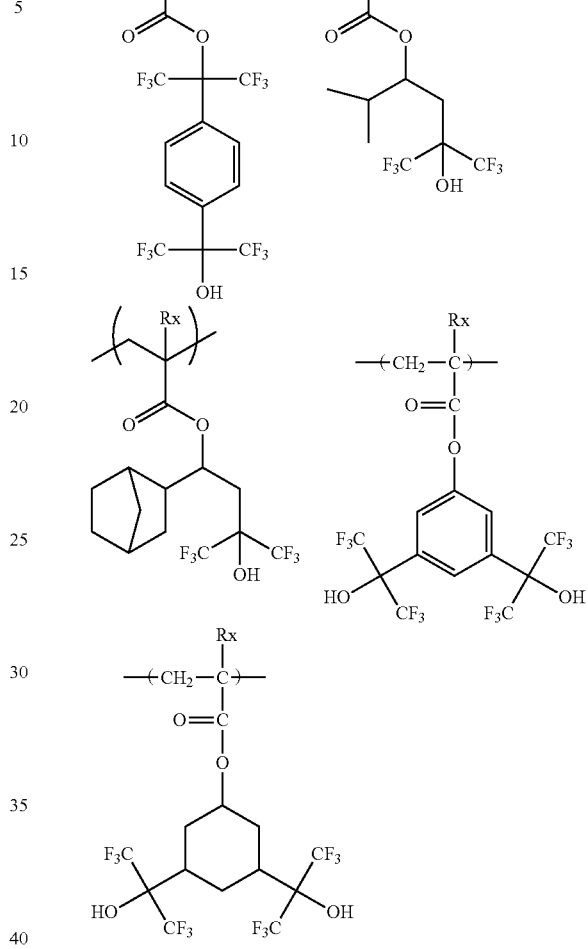

In a case where the resin (X) includes the repeating unit Y4, the content of the repeating unit Y4 is preferably 5% to 80% by mass, more preferably 5% to 70% by mass, and still more preferably 10% to 60% by mass, with respect to all the repeating units in the resin (A).

The resin (X) can be synthesized in accordance with an ordinary method (for example, radical polymerization).

The weight-average molecular weight of the resin (X) is preferably 2,500 to 30,000, more preferably 3,500 to 25,000, still more preferably 4,000 to 10,000, and particularly preferably 4,000 to 8,000. The dispersity (Mw/Mn) is usually 1.0 to 3.0, preferably 1.0 to 2.6, more preferably 1.0 to 2.0, and still more preferably 1.1 to 2.0.

The resin (X) may be used singly or in combination of two or more kinds thereof.

The content of the resin (X) in the composition of the embodiment of the present invention is generally 20% by mass or more in many cases, and is preferably 40% by mass or more, more preferably 50% by mass or more, and still more preferably 60% by mass or more, with respect to the total solid content of the composition. An upper limit thereof is not particularly limited, but is preferably 99.9% by mass or less, more preferably 99.5% by mass or less, and still more preferably 99.0% by mass or less.

<Acid Diffusion Control Agent>

The composition of the embodiment of the present invention preferably includes an acid diffusion control agent. The acid diffusion control agent acts as a quencher that suppresses a reaction of the acid-decomposable resin in the unexposed area by excessive generated acids by trapping the acids generated from a photoacid generator and the like upon exposure. For example, a basic compound (DA), a compound (DB) whose basicity is reduced or lost upon irradiation with actinic rays or radiation, or the like can be used as the acid diffusion control agent.

As the basic compound (DA), compounds having structures represented by Formulae (A) to (E) are preferable.

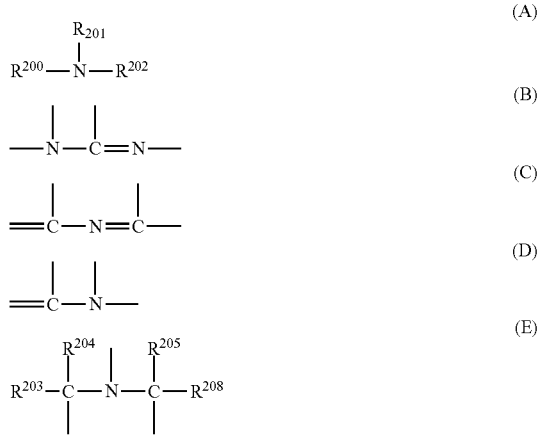

In General Formulae (A) and (E), $R^{200}$, $R^{201}$, and $R^{202}$ each independently represent a hydrogen atom, an alkyl group (preferably having 1 to 20 carbon atoms), a cycloalkyl group (preferably having 3 to 20 carbon atoms), or an aryl group (preferably having 6 to 20 carbon atoms). $R^{201}$ and $R^{202}$ may be bonded to each other to form a ring.

In General Formula (E), $R^{203}$, $R^{204}$, $R^{205}$, and $R^{206}$ each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl groups in each of General Formulae (A) and (E) are more preferably unsubstituted.

As the basic compound (DA), guanidine, aminopyrrolidine, pyrazole, pyrazoline, piperazine, aminomorpholine, aminoalkylmorpholine, piperidine, or the like is preferable; and a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, and an aniline derivative having a hydroxyl group and/or an ether bond, or the like is more preferable.

Examples of the compound having an imidazole structure include imidazole, 2,4,5-triphenylimidazole, and benzimidazole.

Examples of the compound having a diazabicyclo structure include 1,4-diazabicyclo[2,2,2]octane, 1,5-diazabicyclo[4,3,0]non-5-ene, and 1,8-diazabicyclo[5,4,0]undec-7-ene.

Examples of the compound having an onium hydroxide structure include triarylsulfonium hydroxide, phenacylsulfonium hydroxide, and sulfonium hydroxide having a 2-oxoalkyl group (specifically triphenylsulfonium hydroxide, tris(t-butylphenyl)sulfonium hydroxide, bis(t-butylphenyl)iodonium hydroxide, phenacylthiophenium hydroxide, and 2-oxopropylthiophenium hydroxide).

The compound having an onium carboxylate structure is a compound formed by carboxylation of an anionic moiety of a compound having an onium hydroxide structure, and examples thereof include acetate, adamantane-1-carboxylate, and perfluoroalkyl carboxylate. Examples of the compound having a trialkylamine structure include tri(n-butyl)amine and tri(n-octyl)amine.

Examples of the compound having an aniline structure or a pyridine structure include 2,6-diisopropylaniline, N,N-dimethylaniline, N,N-dibutylaniline, and N,N-dihexylaniline. Examples of the alkylamine derivative having a hydroxyl group and/or an ether bond include ethanolamine, diethanolamine, triethanolamine, and tris(methoxyethoxyethyl)amine.

Examples of the aniline derivative having a hydroxyl group and/or an ether bond include N,N-bis(hydroxyethyl)aniline.

Moreover, a superorganic base can also be used as the basic compound (DA).

Examples of the superorganic base include guanidine bases such as tetramethylguanidine and polyguanidine (including guanidine and guanidine derivatives such as substituted forms thereof and polyguanides), amidine-based and guanidine-based polynitrogen polyheterocyclic compounds and polymer-supported strong bases thereof, typified by diazabicyclononene (DBN), diazabicycloundecene (DBU), triazabicyclodecene (TBD), N-methyl-triazabicyclodecene (MTBD), and the like, phosphazene-based (Schweisinger) bases, and proazaphosphatran (Verkade) bases.

Moreover, as the basic compound (DA), an amine compound and an ammonium salt compound can also be used.

Examples of the amine compound include primary, secondary, and tertiary amine compounds, and the amine compound is preferably an amine compound in which at least one or more alkyl groups (preferably having 1 to 20 carbon atoms) are bonded to nitrogen atoms, and more preferably the tertiary amine compound among those.

Furthermore, in a case where the amine compound is the secondary or tertiary amine compound, examples of a group bonded to the nitrogen atom in the amine compound include, in addition to the above-described alkyl groups, a cycloalkyl group (preferably having 3 to 20 carbon atoms) and an aryl group (preferably having 6 to 12 carbon atoms).

In addition, the amine compound preferably includes an oxyalkylene group. The number of the oxyalkylene groups contained in the amine compounds within the molecule is preferably 1 or more, more preferably 3 to 9, and still more preferably 4 to 6. Among those oxyalkylene groups, an oxyethylene group (—CH$_2$CH$_2$O—) or an oxypropylene group (—CH(CH$_3$)CH$_2$O— or —CH$_2$CH$_2$CH$_2$O—) is preferable, and the oxyethylene group is more preferable.

Examples of the ammonium salt compound include primary, secondary, tertiary, and quaternary ammonium salt compounds, and an ammonium salt compound in which one or more alkyl groups are bonded to a nitrogen atom is preferable.

Furthermore, in a case where the ammonium salt compound is a secondary, tertiary, or quaternary ammonium salt compound, examples of a group which is bonded to a nitrogen atom in the ammonium salt compound include, in addition to the above-described alkyl groups, a cycloalkyl group (preferably having 3 to 20 carbon atoms) and an aryl group (preferably having 6 to 12 carbon atoms).

In addition, the ammonium salt compound preferably includes an oxyalkylene group. The number of the oxyalkylene groups is preferably 1 or more, more preferably 3 to 9, and still more preferably 4 to 6 within the molecule. Among those oxyalkylene groups, an oxyethylene group ($—CH_2CH_2O—$) or an oxypropylene group ($—CH(CH_3)CH_2O—$ or $—CH_2CH_2CH_2O—$) is preferable, and the oxyethylene group is more preferable.

Examples of the anion of the ammonium salt compound include a halogen atom, a sulfonate, a borate, and a phosphate, and among these, the halogen atom or the sulfonate is preferable.

As the halogen atom, a chlorine atom, a bromine atom, or an iodine atom is preferable.

As the sulfonate, an organic sulfonate having 1 to 20 carbon atoms is preferable, and preferred specific examples thereof include alkyl sulfonate and aryl sulfonate, having 1 to 20 carbon atoms. The alkyl group of the alkyl sulfonate may have a substituent, and examples of the substituent include a fluorine atom, a chlorine atom a bromine atom, an alkoxy group, an acyl group, and an aromatic ring group. Examples of the alkyl sulfonate include methanesulfonate, ethanesulfonate, butanesulfonate, hexanesulfonate, octanesulfonate, benzyl sulfonate, trifluoromethanesulfonate, pentafluoroethanesulfonate, and nonafluorobutanesulfonate. In addition, examples of the aryl group of the aryl sulfonate include a benzene ring group, a naphthalene ring group, and an anthracene ring group. As the substituent which can be contained in the benzene ring group, the naphthalene ring group, and the anthracene ring group, a linear or branched alkyl group having 1 to 6 carbon atoms (which may be linear or branched) or a cycloalkyl group having 3 to 6 carbon atoms is preferable. Specific examples of the alkyl group and the cycloalkyl group include a methyl group, an ethyl group, an n-propyl group, an isopropyl group, an n-butyl group, an i-butyl group, a t-butyl group, an n-hexyl group, and a cyclohexyl group.

The alkyl group and the cycloalkyl group may have another substituent, and examples of such another substituent include an alkoxy group having 1 to 6 carbon atoms, a halogen atom, a cyano group, a nitro group, an acyl group, and an acyloxy group.

Moreover, as the basic compound (DA), an amine compound having a phenoxy group and an ammonium salt compound having a phenoxy group can also be used.

The amine compound having a phenoxy group and the ammonium salt compound having a phenoxy group are each a compound having a phenoxy group at the terminal on the opposite side to the nitrogen atom of the alkyl group which is contained in the amine compound or the ammonium salt compound.

Examples of a substituent of the phenoxy group include an alkyl group, an alkoxy group, a halogen atom, a cyano group, a nitro group, a carboxyl group, a carboxylic acid ester group, a sulfonic acid ester group, an aryl group, an aralkyl group, an acyloxy group, and an aryloxy group. The substitution position of the substituent may be any of 2- to 6-positions. The number of the substituents may be any one of 1 to 5.

The amine compound having a phenoxy group and the ammonium salt compound having a phenoxy group each preferably have at least one oxyalkylene group between the phenoxy group and the nitrogen atom. The number of the oxyalkylene groups within the molecule is preferably 1 or more, more preferably 3 to 9, and still more preferably 4 to 6. Among oxyalkylene groups, an oxyethylene group ($—CH_2CH_2O—$) or an oxypropylene group ($—CH(CH_2)CH_2O—$ or $—CH_2CH_2CH_2O—$) is preferable, and the oxyethylene group is more preferable.

The amine compound having a phenoxy group can be obtained by heating a mixture of a primary or secondary amine having a phenoxy group and a haloalkyl ether to perform a reaction, then adding an aqueous solution of a strong base (for example, sodium hydroxide, potassium hydroxide, and tetraalkylammonium) to a reaction system, and extracting the reaction product with an organic solvent (for example, ethyl acetate and chloroform). Alternatively, the amine compound having a phenoxy group can also be obtained by heating a mixture of a primary or secondary amine and a haloalkyl ether having a phenoxy group at the terminal to perform a reaction, then adding an aqueous solution of a strong base to the reaction system, and extracting the reaction product with an organic solvent.

The compound (DB) whose basicity is reduced or lost upon irradiation with actinic rays or radiation (hereinafter also referred to as a "compound (DB)") is a compound which has a proton-accepting functional group, and decomposes under irradiation with actinic rays or radiation to exhibit deterioration in proton-accepting properties, no proton-accepting properties, or a change from the proton-accepting properties to acidic properties.

The proton-accepting functional group refers to a functional group having a group or an electron which is capable of electrostatically interacting with a proton, and for example, means a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following general formula.

꾳 꾳 ๑ Unshared electron pair

Preferred examples of the partial structure of the proton-accepting functional group include a crown ether structure, an azacrown ether structure, primary to tertiary amine structures, a pyridine structure, an imidazole structure, and a pyrazine structure.

The compound (DB) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease in the equilibrium constant at chemical equilibrium in a case where a proton adduct is generated from the compound (DB) having the proton-accepting functional group and the proton.

The proton-accepting properties can be confirmed by performing pH measurement.

With regard to specific examples of the compound (DB), reference can be made to those described in paragraphs <0421> to <0428> of JP2014-041328A or paragraphs <0108> to <0116> of JP2014-134686A, the contents of which are incorporated herein by reference.

Specific examples of the basic compound (DA) and the compound (DB) are shown below; but the present invention is not limited.

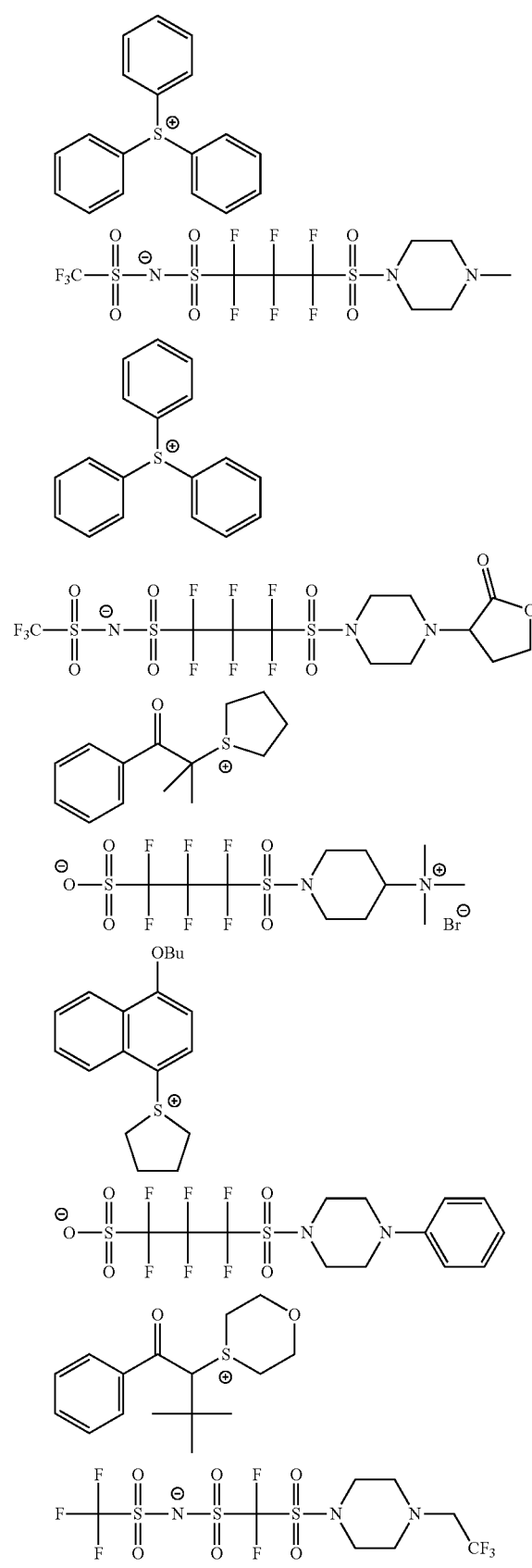
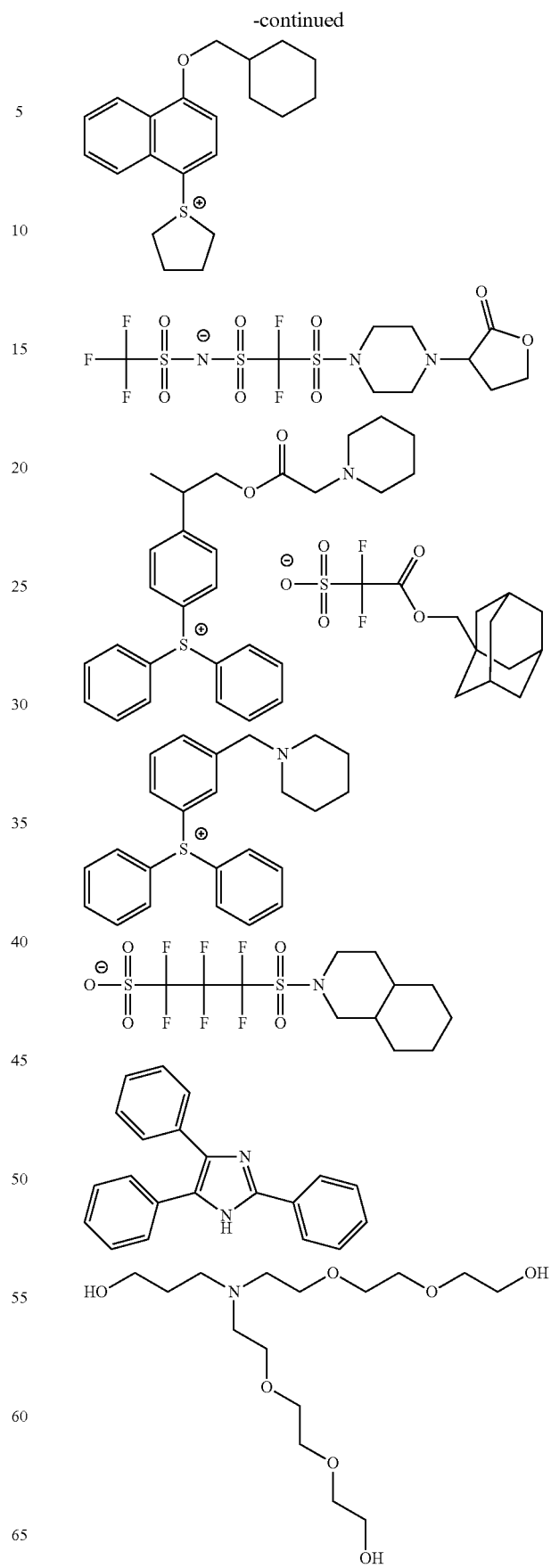

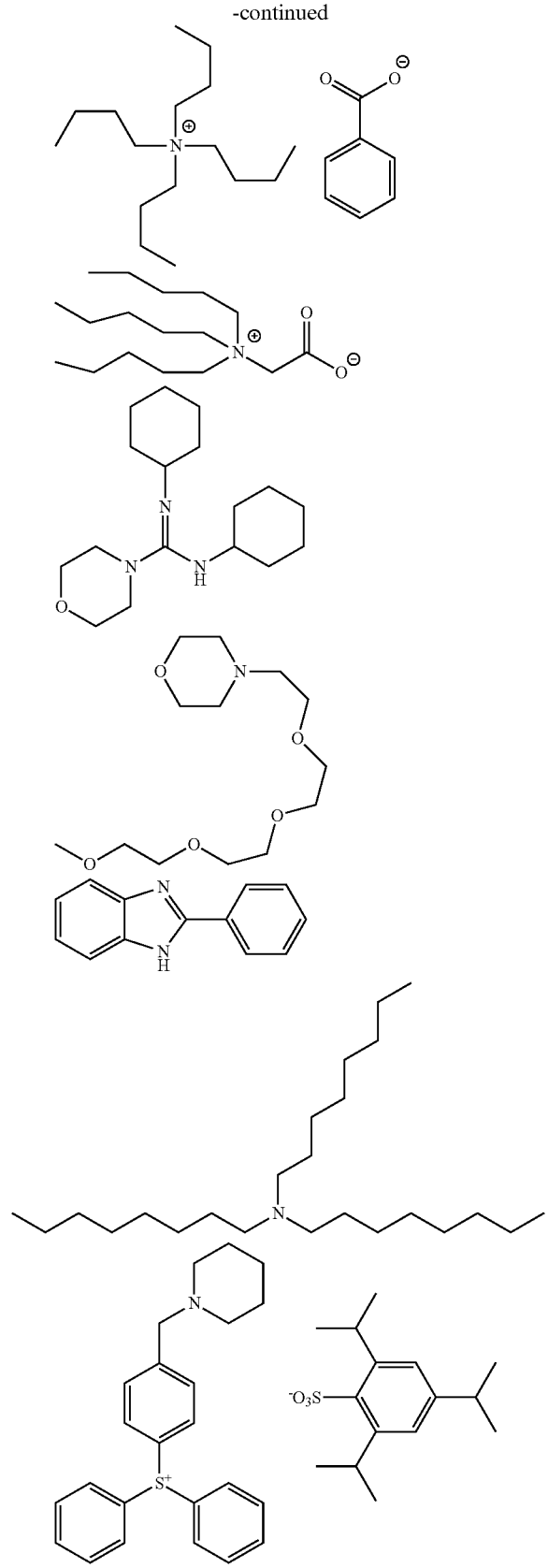

The acid diffusion control agents may be used singly or in combination of two or more kinds thereof.

The content of the acid diffusion control agent (a total content in a case where a plurality of the acid diffusion control agents are present) in the composition of the embodiment of the present invention is preferably 0.001% to 10% by mass, and more preferably 0.01% to 7% by mass, with respect to the total solid content of the composition.

Moreover, as the acid diffusion control agent, for example, the compounds (amine compounds, amido group-containing compounds, urea compounds, nitrogen-containing heterocyclic compounds, and the like) described in paragraphs <0140> to <0144> of JP2013-011833A can also be used.

<Surfactant>

The composition of the embodiment of the present invention may include a surfactant. By incorporating the surfactant into the composition, it is possible to provide a resist pattern having improved adhesiveness and less development defects with good sensitivity and resolution in a case where an exposure light source at a wavelength of 250 nm or less, and particularly 220 nm or less is used.

As the surfactant, fluorine-based and/or silicon-based surfactants are preferable.

Examples of the fluorine-based and/or silicon-based surfactants include the surfactants described in paragraph <0276> in US2008/0248425A. In addition, EFTOP EF301 and EF303 (manufactured by Shin-Akita Chemical Co., Ltd.); FLUORAD FC430, 431, and 4430 (manufactured by Sumitomo 3M Inc.); MEGAFACE F171, F173, F176, F189, F113, F110, F177. F120, and R08 (manufactured by DIC Corp.); SURFLON S-382, SC101, 102, 103, 104, 105, and 106 (manufactured by Asahi Glass Co., Ltd.), TROYSOL S-366 (manufactured by Troy Chemical Corp.), GF-300 and GF-150 (manufactured by Toagosei Chemical Industry Co., Ltd.); SURFLON S-393 (manufactured by Seimi Chemical Co., Ltd.); EFTOP EF121, EF122A, EF122B, RF122C, EF125M, EF135M, EF351, EF352, EF801, EF802, and EF601 (manufactured by JEMCO Inc.); PF636, PF656, PF6320, and PF6520 (manufactured by OMNOVA Solutions Inc.); KH-20 (manufactured by Asahi Kasei Co., Ltd.); or FTX-204G, 208G. 218G, 230G, 204D. 208D, 212D, 218D. and 222D (manufactured by NEOS Co., Ltd.) may be used. In addition, a polysiloxane polymer KP-341 (manufactured by Shin-Etsu Chemical Co., Ltd.) can also be used as the silicon-based surfactant.

Moreover, in addition to the known surfactants as shown above, a surfactant may be synthesized using a fluoroaliphatic compound manufactured using a telomerization method (also referred to as a telomer method) or an oligomerization method (also referred to as an oligomer method). Specifically, a polymer including a fluoroaliphatic group derived from fluoroaliphatic compound may be used as the surfactant. This fluoroaliphatic compound can be synthesized, for example, by the method described in JP2002-090991A.

In addition, a surfactant other than the fluorine-based surfactant and/or the silicon-based surfactants described in paragraph <0280> of US2008/0248425A may be used.

These surfactants may be used singly or in combination of two or more kinds thereof.

The content of the surfactant in the composition of the embodiment of the present invention is preferably 0.0001% to 2% by mass, and more preferably 0.0005% to 1% by mass, with respect to the total solid content of the composition.

<Solvent>

The composition of the embodiment of the present invention may include a solvent (resist solvent).

The solvent preferably includes at least any one of the following component (M1) or the following component (M2), and among these, the solvent more preferably includes the following component (M1).

In a case where the solvent includes the following component (M1), it is preferable that the solvent includes substantially only the component (M1) or is a mixed solvent including at least the component (M1) and the component (M2).

Hereinafter, the component (M1) and the component (M2) will be shown.

Component (M1): Propylene glycol monoalkyl ether carboxylate

Component (M2): A solvent selected from the following component (M2-1) or a solvent selected from the following component (M2-2)

Component (M2-1): Propylene glycol monoalkyl ether, lactic acid ester, acetic acid ester, butyl butyrate, alkoxy propionic acid ester, chained ketone, cyclic ketone, lactone, or alkylene carbonate Component (M2-2): Another solvent having a flash point (also referred to as fp) of 37° C. or higher.

In a case where the solvent and the above-described resin (X) are used in combination, the coating property of the composition is improved and a pattern having a less number of development defects is obtained. Although a reason therefor is not necessarily clear, it is considered that the solvent has a good balance among the solubility, the boiling point, and the viscosity of the above-described resin (X), and therefore, unevenness in the film thickness of a resist film, generation of precipitates during spin coating, and the like can be suppressed.

As the component (M1), at least one selected from the group consisting of propylene glycol monomethyl ether acetate (PGMEA), propylene glycol monomethyl ether propionate, and propylene glycol monoethyl ether acetate is preferable, and the propylene glycol monomethyl ether acetate (PGMEA) is more preferable.

As the component (M2-1), the following ones are preferable.

As the propylene glycol monoalkyl ether, propylene glycol monomethyl ether (PGME) or propylene glycol monoethyl ether is preferable.

As the lactic acid ester, ethyl lactate, butyl lactate, or propyl lactate is preferable.

As the acetic acid ester, methyl acetate, ethyl acetate, butyl acetate, isobutyl acetate, propyl acetate, isoamyl acetate, methyl formate, ethyl formate, butyl formate, propyl formate, or 3-methoxybutyl formate is preferable.

As the alkoxy propionic acid ester, methyl 3-methoxypropionate (MMP), or ethyl 3-ethoxypropionate (EEP) is preferable.

As the chained ketone, 1-octanone, 2-octanone, 1-nonanone, 2-nonanone, acetone, 2-heptanone, 4-heptanone, 1-hexanone, 2-hexanone, diisobutyl ketone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, or methyl amyl ketone is preferable.

As the cyclic ketone, methyl cyclohexanone, isophorone, or cyclohexanone is preferable.

As the lactone, γ-butyrolactone is preferable.

As the alkylene carbonate, propylene carbonate is preferable.

As the component (M2-1), propylene glycol monomethyl ether (PGME), ethyl lactate, ethyl 3-ethoxypropionate, methyl amyl ketone, cyclohexanone, butyl acetate, pentyl acetate, γ-butyrolactone, or propylene carbonate is more preferable.

Specific examples of the component (M2-2) include propylene glycol monomethyl ether (fp: 47° C.), ethyl lactate (fp: 53° C.), ethyl 3-ethoxypropionate (fp: 49° C.), methyl amyl ketone (fp: 42° C.), cyclohexanone (fp: 44° C.), pentyl acetate (fp: 45° C.), methyl 2-hydroxyisobutyrate (fp: 45° C.), γ-butyrolactone (fp: 101° C.), and propylene carbonate (fp: 132° C.). Among those, propylene glycol monoethyl ether, ethyl lactate, pentyl acetate, or cyclohexanone is preferable, and propylene glycol monoethyl ether or ethyl lactate is more preferable.

In addition, the "flash point (fp)" herein means the value described in a reagent catalog of Tokyo Chemical Industry Co., Ltd. or Sigma-Aldrich Co. LLC.

The mixing ratio (mass ratio: M1/M2) of the component (M1) to the component (M2) is preferably 100/0 to 15/85, more preferably in the range of 100/0 to 40/60, and still more preferably in the range of 100/0 to 60/40, from the viewpoint that the number of development defects is further decreased.

Moreover, the solvent may include solvents other than the component (M1) and the component (M2). In this case, the content of the solvents other than the components (M1) and (M2) is preferably 5% to 300/o by mass with respect to the total mass of the solvent.

Examples of such other solvents include ester-based solvents having 7 or more carbon atoms (preferably 7 to 14 carbon atoms, more preferably 7 to 12 carbon atoms, and still more preferably 7 to 10 carbon atoms) and 2 or less heteroatoms. Furthermore, the ester-based solvents having 7 or more carbon atoms and 2 or less heteroatoms do not include solvents corresponding to the above-described component (M2).

As the ester-based solvents having 7 or more carbon atoms and 2 or less heteroatoms, amyl acetate, 2-methylbutyl acetate, 1-methylbutyl acetate, hexyl acetate, pentyl propionate, hexyl propionate, butyl propionate, isobutyl isobutyrate, heptyl propionate, butyl butanoate, or the like is preferable, and isoamyl acetate is more preferable.

<Other Additives>

The composition of the embodiment of the present invention may further include a hydrophobic resin, a dissolution inhibiting compound (a compound whose solubility in an organic developer decreases through decomposition by the action of an acid, with a molecular weight thereof being preferably 3,000 or less), a dye, a plasticizer, a light sensitizer, a light absorber, and/or a compound that accelerates dissolution in a developer (for example, a phenol compound having a molecular weight of 1,000 or less, or an alicyclic or aliphatic compound including a carboxyl group).

<Preparation Method>

The concentration of the solid content in the composition of the embodiment of the present invention is preferably 0.5% to 30% by mass, more preferably 1% to 20% by mass, and still more preferably 1% to 10% by mass, from the viewpoint that the coating property is more excellent. The concentration of the solid content is a mass percentage of other resist components excluding the solvent with respect to the total mass of the composition.

In addition, the film thickness of a resist film (an actinic ray-sensitive or radiation-sensitive film) formed of the composition of the embodiment of the present invention is generally 200 nm or less, and more preferably 100 nm or less, from the viewpoint of improving resolving power. For example, it is preferable that the film thickness of a resist film thus formed is 80 nm or less in order to resolve a 1:1 line-and-space pattern with a line width of 20 nm or less. In a case where the film thickness is 80 nm or less, more excellent resolution performance is obtained due to suppressed pattern collapse upon application of a developing step which will be described later.

A more preferred range of the film thickness is 15 to 60 nm. Such a film thickness can be obtained by setting to the concentration of the solid content in the composition to an appropriate range to provide the composition with a suitable viscosity and improve the coating property or the film forming property.

The composition of the embodiment of the present invention is used by dissolving the components in a predetermined organic solvent (preferably the mixed solvent), and preferably the mixed solvent, and filtering the solution through a filter and applying it onto a predetermined support (substrate). The pore size of a filter for use in filtration through the filter is preferably pore size of 0.1 μm or less, more preferably 0.05 μm or less, and still more preferably 0.03 μm or less. The filter is preferably a polytetrafluoroethylene-made, polyethylene-made, or nylon-made filter. In the filtration through a filter as shown in JP2002-062667A, circulating filtration may be performed or the filtration may be performed by connecting plural kinds of filters in series or in parallel. In addition, the composition may be filtered in plural times. Furthermore, the composition may be subjected to a deaeration treatment or the like before or after filtration through a filter.

<Applications>

The composition of the embodiment of the present invention relates to an actinic ray-sensitive or radiation-sensitive resin composition whose properties change by undergoing a reaction upon irradiation with actinic rays or radiation. More specifically, the composition of the embodiment of the present invention relates to an actinic ray-sensitive or radiation-sensitive resin composition which is used in a step of manufacturing a semiconductor such as an integrated circuit (IC), for manufacture of a circuit board for a liquid crystal, a thermal head, or the like, the manufacture of a mold structure for imprinting, other photofabrication steps, or production of a planographic printing plate or an acid-curable composition. A pattern formed in the present invention can be used in an etching step, an ion implantation step, a bump electrode forming step, a rewiring forming step, a microelectromechanical system (MEMS), or the like.

[Pattern Forming Method and Resist Film]

The present invention also relates to a pattern forming method using the actinic ray-sensitive or radiation-sensitive resin composition. Hereinafter, the pattern forming method of the embodiment of the present invention will be described. In addition, the resist film of the embodiment of the present invention will also be described, together with the pattern forming method.

The pattern forming method of the embodiment of the present invention includes:

(i) a step of forming a resist film (actinic ray-sensitive or radiation-sensitive film) on a support with the above-described actinic ray-sensitive or radiation-sensitive resin composition (resist film forming step), (ii) a step of exposing the resist film (irradiating actinic rays or radiation) (exposing step), and (iii) a step of developing the exposed resist film with a developer (developing step).

The pattern forming method of the embodiment of the present invention is not particularly limited as long as it includes the steps (i) to (iii), and may further include the following steps.

In the pattern forming method of the embodiment of the present invention, the exposing method in the exposing step (ii) may be liquid immersion exposure.

The pattern forming method of the embodiment of the present invention preferably includes a prebaking (PB) step (iv) before the exposing step (ii).

The pattern forming method of the embodiment of the present invention preferably includes a post-exposure baking (PEB) step (v) after the exposing step (ii) and before the developing step (iii).

The pattern forming method of the embodiment of the present invention may include the exposing step (ii) a plurality of times.

The pattern forming method of the embodiment of the present invention may include the prebaking step (iv) a plurality of times.

The pattern forming method of the embodiment of the present invention may include the post-exposure baking step (v) a plurality of times.

In the pattern forming method of the embodiment of the present invention, the above-described resist film forming step (i), exposing step (ii), and developing step (iii) can be performed by a generally known method.

In addition, a resist underlayer film (for example, spin on glass (SOG), spin on carbon (SOC), and an antireflection film) may be formed between the resist film and the support, as desired. As a material constituting the resist underlayer film, known organic or inorganic materials can be appropriately used.

A protective film (topcoat) may be formed on the upper layer of the resist film. As the protective film, a known material can be appropriately used. For example, the compositions for forming a protective film disclosed in US2007/0178407A, US2008/0085466A. US2007/0275326A, US2016/0299432A, US2013/0244438A, or WO2016/157988A can be suitably used. The composition for forming a protective film preferably includes the above-described acid diffusion control agent.

The film thickness of the protective film is preferably 10 to 200 nm, more preferably 20 to 100 nm, and still more preferably 40 to 80 nm.

The support is not particularly limited, and a substrate which is generally used in a step of manufacturing a semiconductor such as an IC, and a process for manufacturing a circuit board for a liquid crystal, a thermal head, or the like, and other lithographic processes of photofabrication can be used. Specific examples of the support include an inorganic substrate such as silicon, $SiO_2$, and SiN.

For any of the prebaking step (iv) and the post-exposure baking step (v), the baking temperature is preferably 80° C. to 150° C., more preferably 80° C. to 140° C., and still more preferably 80° C. to 130° C.

For any of the prebaking step (iv) and the post-exposure baking step (v), the baking time is preferably 30 to 1,000 seconds, more preferably 60 to 800 seconds, and still more preferably 60 to 600 seconds.

The baking may be performed using a means comprised in an exposure device and a development device, or may also be performed using a hot plate or the like.

A light source wavelength used in the exposing step is not particularly limited, and examples thereof include infrared rays, visible light, ultraviolet rays, far ultraviolet rays, extreme ultraviolet rays (EUV), X-rays, and electron beams. Among those, far ultraviolet rays are preferable, whose wavelength is preferably 250 nm or less, more preferably 220 nm or less, and still more preferably 1 to 200 nm. Specific examples thereof include a KrF excimer laser (248 nm), an ArF excimer laser (193 nm), an $F_2$ excimer laser (157 nm), X-rays, EUV (13 nm), and electron beams, the KrF excimer laser, the ArF excimer laser, EUV, or the electron beams are preferable, and EUV or the electron beams are more preferable.

In the developing step (iii), the developer may be either an alkali developer or a developer including an organic solvent (hereinafter also referred to as an organic developer), but the alkali development is preferable.

As an alkali component included in the alkali developer, a quaternary ammonium salt typified by tetramethylammonium hydroxide is usually used. In addition, an aqueous alkali solution including an alkali component such as an inorganic alkali, primary to tertiary amines, alcohol amines, and cyclic amines can also be used.

Furthermore, the alkali developer may include an appropriate amount of alcohols and/or a surfactant. The alkali concentration of the alkali developer is usually 0.1% to 20% by mass. The pH of the alkali developer is usually 10 to 15.

A time period for performing development the using the alkali developer is usually 10 to 300 seconds.

The alkali concentration, the pH, and the development time using the alkali developer can be appropriately adjusted depending on a pattern formed.

The organic developer is preferably a developer including at least one organic solvent selected from the group consisting of a ketone-based solvent, an ester-based solvent, an alcohol-based solvent, an amide-based solvent, an ether-based solvent, and a hydrocarbon-based solvent.

Examples of the ketone-based solvent include 1-octanone, 2-octanone, 1-nonanone, 2-nonanone, acetone, 2-heptanone (methyl amyl ketone), 4-heptanone. 1-hexanone, 2-hexanone, diisobutyl ketone, cyclohexanone, methylcyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butyrate, methyl 2-hydroxyisobutyrate, isoamyl acetate, isobutyl isobutyrate, and butyl propionate.

As the alcohol-based solvent, the amide-based solvent, the ether-based solvent, and the hydrocarbon-based solvent, the solvents disclosed in paragraphs <0715> to <0718> of US2016/0070167A1 can be used.

A plurality of the solvents may be mixed or the solvent may be used in admixture with a solvent other than those described above or water. The moisture content in the entire developer is preferably less than 50% by mass, more preferably less than 20% by mass, and still more preferably less than 100/o by mass, and particularly preferably, moisture is not substantially included.

The content of the organic solvent with respect to the organic developer is preferably 50% to 100% by mass, more preferably 80% to 100% by mass, still more preferably 90% to 100% by mass, and particularly preferably 95% to 100% by mass, with respect to the total amount of the developer.

The organic developer may include an appropriate amount of a known surfactant, as desired.

The content of the surfactant is usually 0.001% to 5% by mass, preferably 0.005% to 2% by mass, and still more preferably 0.01% to 0.5% by mass, with respect to the total amount of the developer.

The organic developer may include the above-described acid diffusion control agent.

Examples of the developing method include a method in which a substrate is dipped in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), and a method in which a developer is continuously jetted onto a substrate spun at a constant rate while scanning a developer jetting nozzle at a constant rate (a dynamic dispense method).

A combination of a step of performing development using an aqueous alkali solution (an alkali developing step) and a step of performing development using a developer including an organic solvent (an organic solvent developing step) may be used. Thus, a finer pattern can be formed since a pattern can be formed by keeping only a region with an intermediate exposure intensity from not being dissolved.

It is preferable that the method include a step of performing washing using a rinsing liquid (a rinsing step) after the developing step (iii).

As the rinsing liquid used in the rinsing step after the developing step with an alkali developer, for example, pure water can be used. The pure water may include an appropriate amount of a surfactant. In this case, after the developing step or the rinsing step, a treatment for removing the developer or the rinsing liquid adhering on a pattern by a supercritical fluid may be added. In addition, after the rinsing treatment or the treatment using a supercritical fluid, a heating treatment for removing moisture remaining in the pattern may be performed.

The rinsing liquid used in the rinsing step after the developing step with a developer including an organic solvent is not particularly limited as long as the rinsing liquid does not dissolve the resist pattern, and a solution including a common organic solvent can be used. As the rinsing liquid, a rinsing liquid including at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent include the same solvents as those described for the developer including an organic solvent.

As the rinsing liquid used in the rinsing step in this case, a rinsing liquid including a monohydric alcohol is more preferable.

Here, examples of the monohydric alcohol used in the rinsing step include linear, branched, or cyclic monohydric alcohols. Specific examples thereof include 1-butanol, 2-butanol, 3-methyl-1-butanol, tert-butyl alcohol, 1-pentanol, 2-pentanol, I-hexanol, 4-methyl-2-pentanol, 1-heptanol. 1-octanol, 2-hexanol, cyclopentanol, 2-heptanol, 2-octanol, 3-hexanol, 3-heptanol, 3-octanol, 4-octanol, and methyl isobutyl carbinol. Examples of the monohydric alcohol having 5 or more carbon atoms include 1-hexanol, 2-hexanol, 4-methyl-2-pentanol, 1-pentanol, 3-methyl-1-butanol, and methyl isobutyl carbinol.

The respective components in plural number may be mixed or the components may be used in admixture with an organic solvent other than the above solvents.

The moisture content in the rinsing liquid is preferably 10% by mass or less, more preferably 5% by mass or less, and still more preferably 3% by mass or less. By setting the moisture content to 10% by mass or less, good development characteristics are obtained.

The rinsing liquid may include an appropriate amount of a surfactant.

In the rinsing step, the substrate that has been subjected to development using an organic developer is subjected to a washing treatment using a rinsing liquid including an organic solvent. A method for the washing treatment method is not particularly limited, but examples thereof include a method in which a rinsing liquid is continuously jetted on a substrate rotated at a constant rate (a rotation application method), a method in which a substrate is dipped in a tank filled with a rinsing liquid for a certain period of time (a dip method), and a method in which a rinsing liquid is sprayed on a substrate surface (a spray method). Among those, it is preferable that a washing treatment is carried out using the rotation application method, and a substrate is rotated at a rotation speed of 2,000 to 4,000 rpm after washing, thereby removing the rinsing liquid from the substrate. Furthermore, it is also preferable that the method includes a baking step after the rinsing step (post-baking). The developer and the rinsing liquid remaining between and inside the patterns are removed by the baking step. In the baking step after the rinsing step, the heating temperature is usually 40° C. to 160° C., and preferably 70° C. to 95° C., and typically for 10 seconds to 3 minutes, and preferably for 30 to 90 seconds.

It is preferable that various materials (for example, a resist solvent, a developer, a rinsing liquid, a composition for forming an antireflection film, and a composition for forming a topcoat) used in the actinic ray-sensitive or radiation-sensitive resin composition of the embodiment of the present invention, and the pattern forming method of the embodiment of the present invention do not include impurities such as metals, components, isomers, and residual monomers. The content of the impurities included in these materials is preferably 1 ppm or less, more preferably 100 ppt or less, and still more preferably 10 ppt or less, and particularly preferably, the impurities are not substantially included (no higher than a detection limit of a measurement device).

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a polytetrafluoroethylene-made, polyethylene-made, or nylon-made filter is preferable. As the filter, a filter which has been washed with an organic solvent in advance may be used. In the step of filtration using a filter, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step. As the filter, a filter having a reduced amount of elutes as disclosed in JP2016-201426A is preferable.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used. Examples of the metal adsorbing agent include those disclosed in JP2016-206500A.

In addition, as a method for reducing the impurities such as metals included in the various materials, metal content selects the less material as a raw material constituting the various materials, performing filtering using a filter of the raw material constituting the various materials, equipment the inner and a method such as performing distillation under conditions suppressing as much as possible equal to contamination is lined with TEFLON (registered trademark). Preferred conditions in the filtering using a filter to be performed on the raw material constituting the various materials are similar to the above-described conditions.

In order to prevent impurities from being incorporated, it is preferable that various materials are stored in the container described in US2015/0227049A, JP2015-123351A, or the like.

A method for improving the surface roughness of a pattern may be applied to a pattern formed by the pattern forming method of the embodiment of the present invention. Examples of the method for improving the surface roughness of a pattern include the method of treating a pattern by plasma of a hydrogen-containing gas, as disclosed in US2015/0104957A. In addition, known methods as described in JP2004-235468A, US2010/0020297A, and Proc. of SPIE Vol. 832883280N-1 "EUV Resist Curing Technique for LWR Reduction and Etch Selectivity Enhancement" may be applied.

In addition, a pattern formed by the method can be used as a core material (core) of the spacer process disclosed in, for example, JP1991-270227A (JP-H03-270227A) and US2013/0209941A.

[Method for Manufacturing Electronic Device]

Moreover, the present invention further relates to a method for manufacturing an electronic device, the method including the above-described pattern forming method. The electronic device manufactured by the method for manufacturing an electronic device of an embodiment of the present invention is suitably mounted on electric or electronic equipment (for example, home electronics, office automation (OA)-related equipment, media-related equipment, optical equipment, and telecommunication equipment).

EXAMPLES

Hereinbelow, the present invention will be described in more detail with reference to Examples. The materials, the amounts of materials used, the proportions, the treatment details, the treatment procedure, and the like shown in the Examples below may be modified as appropriate as long as the modifications do not depart from the spirit of the present invention. Therefore, the scope of the present invention should not be construed as being limited to the Examples shown below.

<Resin>

The respective repeating units in resins P001 to P003 shown in Table 1 are shown below.

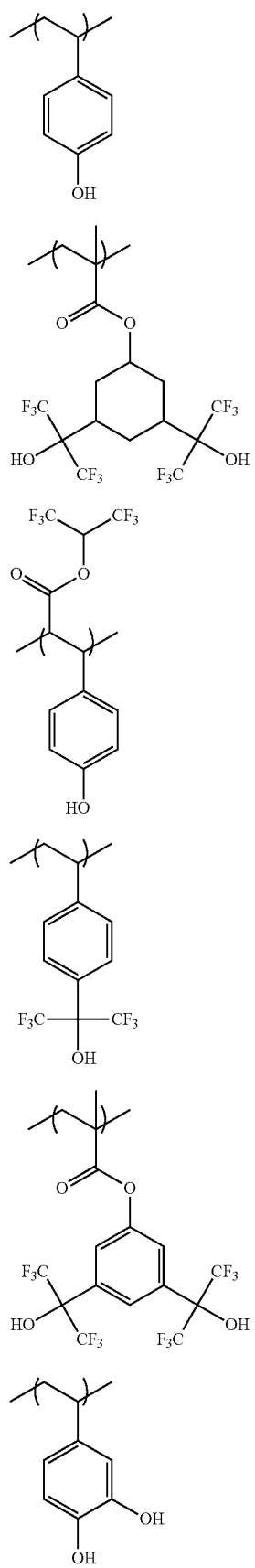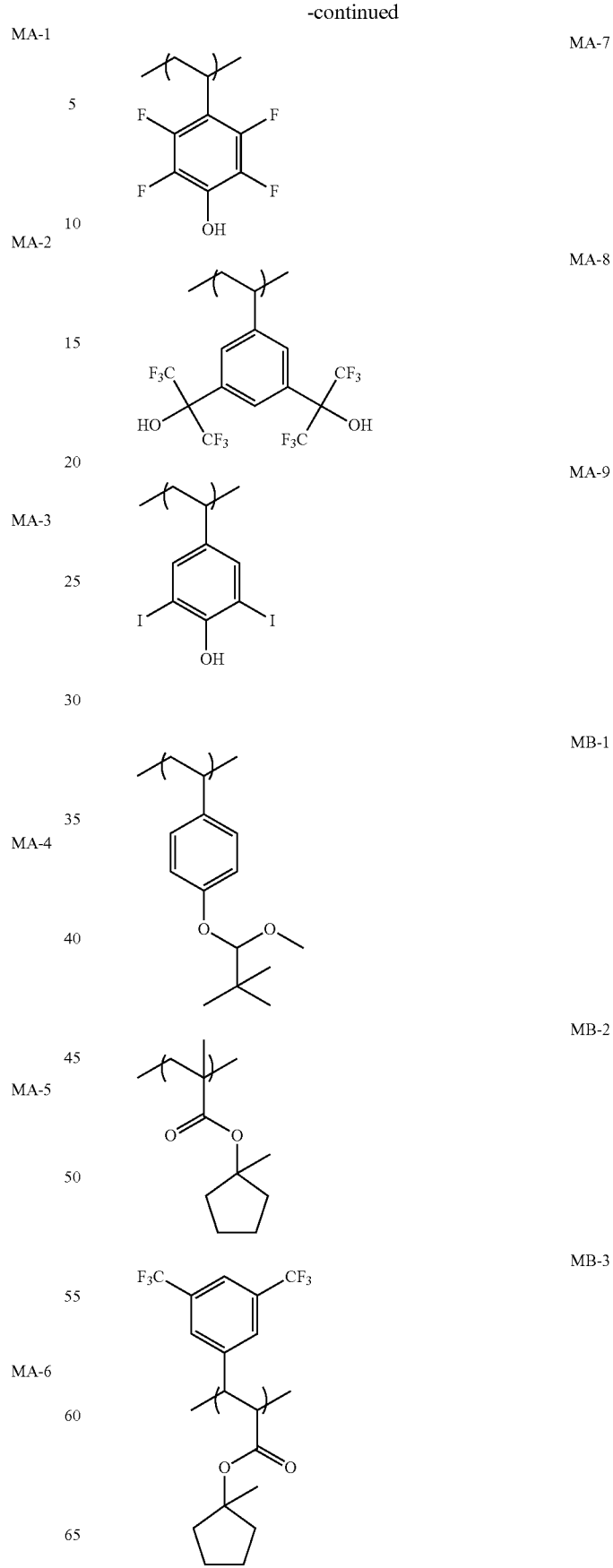

MB-4
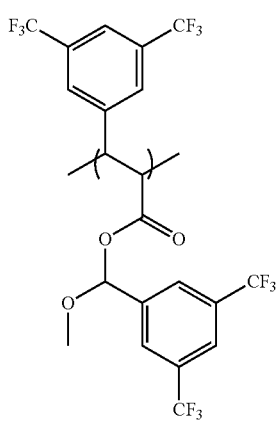
MB-5
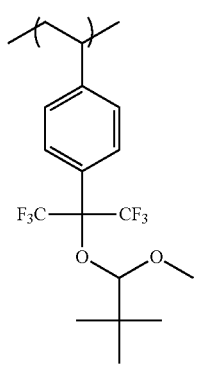
MB-6
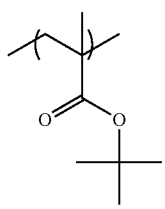
MB-7
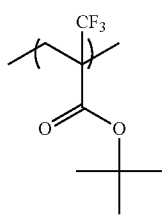
MB-8
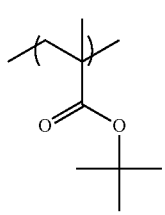
MC-1
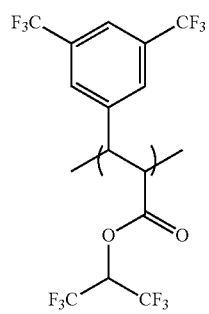
MC-2
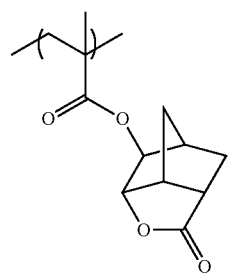
MC-3
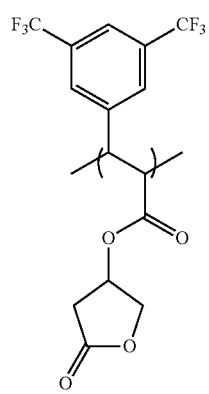
MC-4
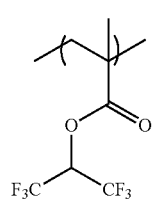
MC-5
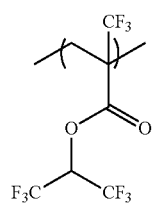

-continued

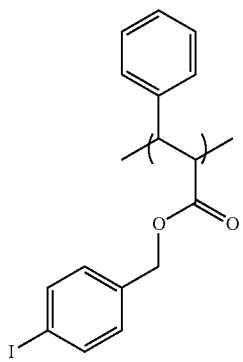
MC-6

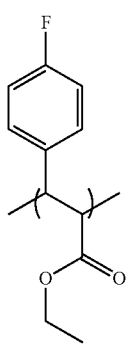
MC-7

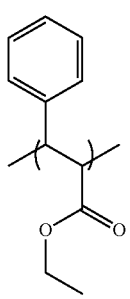
MC-8

The resins shown in Table 1 were synthesized using the monomers. Synthesis Examples are shown below Synthesis Example: Synthesis of Resin P001

10.0 g, 13.3 g, and 10.0 g of monomers respectively corresponding to the repeating units (MA-2/MB-1/MC-2 in the order from the left side) of the resin P001 and a polymerization initiator V-601 (4.61 g) were dissolved in cyclohexanone (54.6 g). A solution thus obtained was taken as a monomer solution.

Cyclohexanone (23.4 g) was put into a reaction container and the monomer solution was added dropwise to the reaction container whose a system had been adjusted to 85° C., for 4 hours under a nitrogen gas atmosphere. The obtained reaction solution was stirred at 85° C. for 2 hours in the reaction container and then left to be cooled until the temperature reached room temperature.

The reaction solution after being left to be cooled was added dropwise to a mixed liquid of methanol and water (methanol/water=5/5 (mass ratio)) for 20 minutes, and the precipitated powder was collected by filtration. The obtained powder was dried to obtain the resin P001 (21.6 g).

The compositional ratio (mass ratio) of the repeating units determined by a nuclear magnetic resonance (NMR) method was 30/40/30. Furthermore, the weight-average molecular weight (Mw) in terms of polystyrene as a standard and the dispersity (Mw/Mn) were 5,300 and 1.6, respectively. In addition, the weight-average molecular weight (Mw) and the dispersity (Mw/Mn) were measured by gel permeation chromatography (GPC) (carrier: tetrahydrofuran (THF)).

Synthesis Example: Synthesis of the Other Resins

The other resins were synthesized by the same procedure as for the resin P001 or by the procedure in the related art.

The repeating units, the compositional ratios (mass ratios), the weight-average molecular weights (Mw), and the dispersities (Mw/Mn) of the respective resins are shown in Table 1. The compositional ratios correspond to the respective repeating units in the order from the left side.

TABLE 1

| | Repeating unit | Compositional ratio (mass ratio) | Weight-average molecular weight | Dispersity |
|---|---|---|---|---|
| P001 | MA-2/MB-1/MC-2 | 30/40/30 | 5,300 | 1.6 |
| P002 | MA-1/MB-4/MC-3 | 35/35/30 | 4,800 | 1.5 |
| P003 | MA-8/MB-3/MC-1 | 30/40/30 | 5,100 | 1.6 |

<Photoacid Generator>

The structures of the photoacid generators shown in Table 2 are shown below. In addition, the cationic moieties and the anionic moieties of the photoacid generators are each individually shown below.

<<Anionic Moieties of Photoacid Generators>>

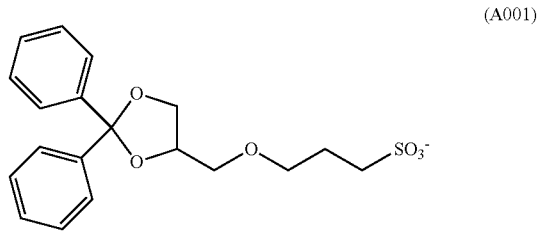
(A001)

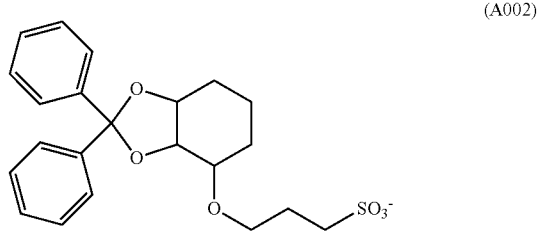
(A002)

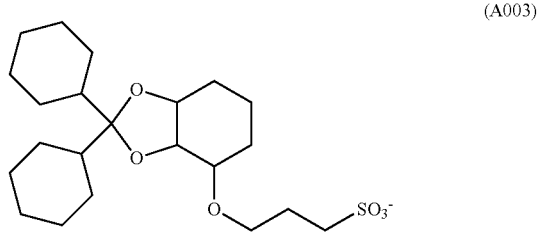
(A003)

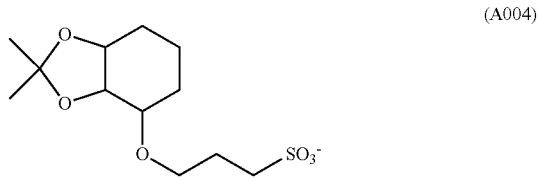
(A004)

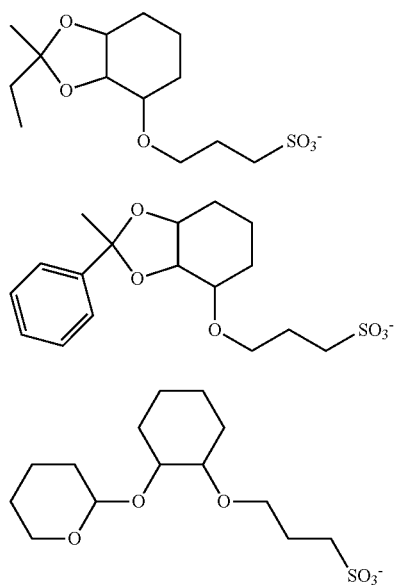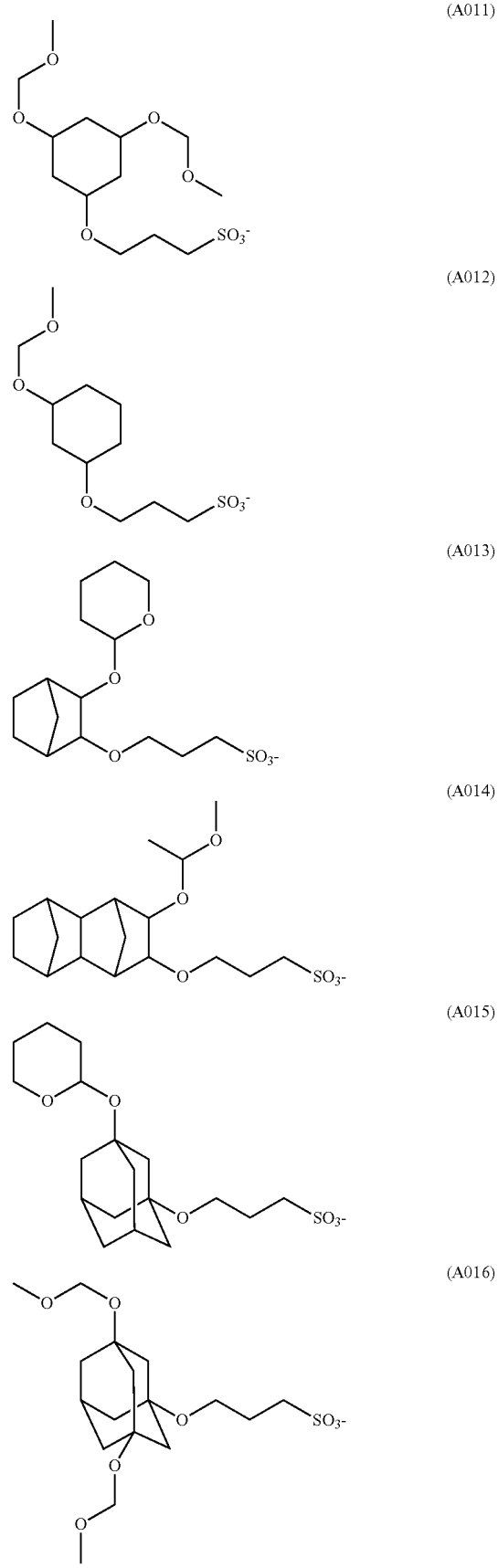

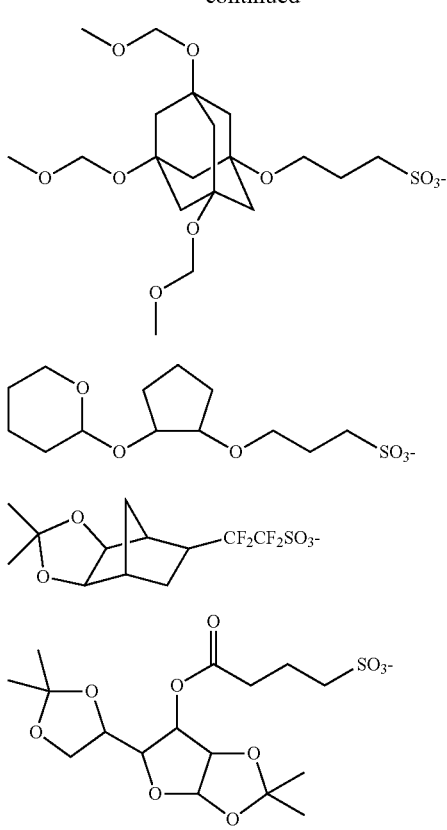

(A017)

(A018)

(A901)

(A902)

<<Synthesis Example of Na Salt of Anionic Moiety>>

The Na salts of the anionic moieties A001 to A018 were synthesized as follows.

(Na Salt of A002)

9.9 g of 1,2,3-cyclohexanetriol, 9.1 g of benzophenone, 0.5 g of p-toluene sulfonic acid monohydrate, and 100 mL of toluene were mixed at room temperature to obtain a mixture 1. The obtained mixture 1 was heated at 110'C and stirred for 10 hours while removing the moisture under reflux to obtain a reaction solution. The obtained reaction solution was cooled to room temperature, 100 mL of a saturated aqueous sodium hydrogen carbonate solution was added thereto, and the mixture was stirred for 5 minutes to obtain a mixture 2. The obtained mixture 2 was left to stand to separate the organic layer. The separated organic layer was combined and concentrated under reduced pressure, and the obtained residue was purified by silica gel column chromatography to obtain 9.7 g of A002-A. $^1$H NMR (DMSO-d6): 7.40-7.55 (m, 4H), 7.30-7.38 (m, 6H), 4.81 (bs, 1H), 4.31 (bs, 1H), 4.04 (bs, 1H), 3.68 (bs, 1H), 1.40-1.70 (m, 4H), 1.15-1.32 (m, 2H). 8.0 g of A002-A and 30 mL of N-methylpyrrolidone were put into a flask and stirred to obtain a solution. 2.2 g of sodium hydride (purity of 60%, oil dispersion) was carefully added to the obtained solution. 3.3 g of 1,3-propanesultone was added dropwise thereto for 10 minutes such that the internal temperature did not exceed 40° C., and then the mixture was stirred for 10 minutes. 150 mL of a 15%-by-mass aqueous sodium acetate solution was added to the solution after stirring to precipitate crystals. The precipitated crystals were separated by filtration. These crystals were dispersed and washed with a mixed solution (1 v/1 v) of 100 mL of hexane/ethyl acetate. These crystals were further dispersed and washed with 50 mL of isopropyl alcohol and then separated by filtration to obtain 8.3 g of A002-Na (Na salt of A002).

$^1$H NMR (DMSO-d6): 7.40-7.55 (m, 4H), 7.30-7.38 (m 6H), 4.32 (bs, 1H), 4.18 (bs, 1H), 3.50 (m, 3H), 2.46 (bs, 2H), 1.79 (bs, 2H), 1.54-1.73 (m, 3H), 1.37-1.55 (m, 1H), 1.13-1.32 (m. 2H)

(Na Salt of A001)

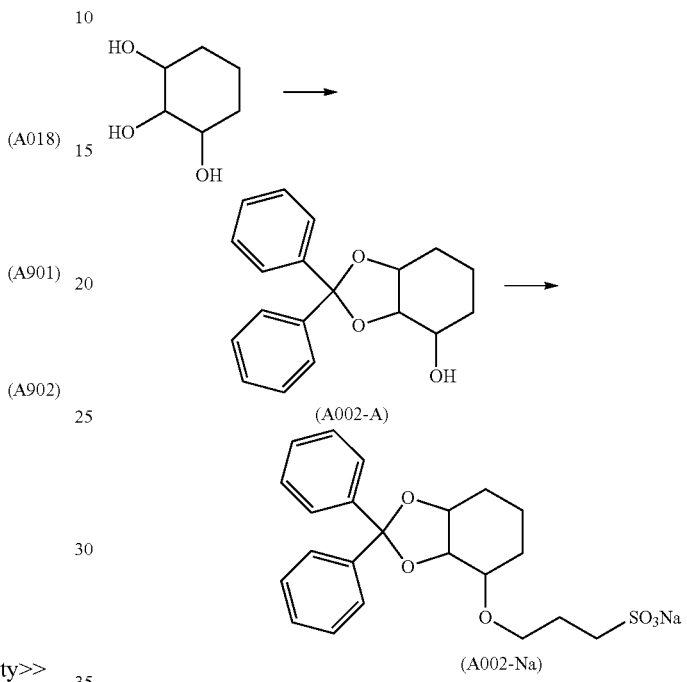

(A002-A)

(A002-Na)

A Na salt of A001 was synthesized by performing a reaction in the same manner as above, except that 1,2,3-cyclohexanetriol was changed to an equimolar amount of glycerin in the synthesis of the Na salt of A002.

(Na Salt of A003)

A Na salt of A003 was synthesized by performing a reaction in the same manner as above, except that benzophenone was changed to an equimolar amount of dicyclohexyl ketone in the synthesis of the Na salt of A002.

(Na Salt of A004)

A Na salt of A004 was synthesized by performing a reaction in the same manner as above, except that benzophenone was changed to an equimolar amount of acetone in the synthesis of the Na salt of A002.

(Na Salt of A005)

A Na salt of A005 was synthesized by performing a reaction in the same manner as above, except that benzophenone was changed to an equimolar amount of methyl ethyl ketone and 1,3-propanesultone was changed to an equimolar amount of 1,4-butanesultone in the synthesis of the Na salt of A002.

(Na Salt of A006)

A Na salt of A006 was synthesized by performing a reaction in the same manner as above, except that benzophenone was changed to an equimolar amount of benzophenone and 1,3-propanesultone was changed to an equimolar amount of 1,4-butanesultone in the synthesis of the Na salt of A002.

(Na Salt of A007)

A Na salt of A007 was synthesized by performing a reaction in the same manner as above, except that 1,2,3- cyclohexanetriol was changed to an equimolar amount of 1,2-cyclohexanediol and benzophenone was changed to an equimolar amount of dihydropyran in the synthesis of the Na salt of A002.

(Na Salt of A008)

13.2 g of 1,2,3-cyclohexanetriol, 5.0 g of sodium hydride (oil dispersion, a content of 60%), and 100 mL of dimethylformamide were mixed at room temperature to obtain a mixture. To the obtained mixture was added 12.2 g of 1,3-propanesultone, and the mixture was heated and stirred at 70° C. for 10 hours to obtain a reaction solution 1. The obtained reaction solution 1 was cooled to room temperature and 5 mL of methanol was carefully added dropwise thereto to obtain a reaction solution 2. The reaction solution 2 was concentrated under reduced pressure and the obtained concentrated was purified by silica gel column chromatography (ethyl acetate/methanol=9/1) to obtain 22.4 g of A008-A.

13.8 g of A008-A and 8.7 g of 2,3-dihydropyran were added to 100 mL of acetonitrile to obtain a solution. To the obtained solution was added 0.1 g of p-toluene sulfonic acid monohydrate, and the mixture was stirred for 10 hours to obtain a reaction solution. To the obtained reaction solution was added 5 mL of a saturated aqueous sodium hydrogen carbonate solution, and the mixture was stirred and then concentrated under reduced pressure to obtain a concentrate. The obtained concentrate was purified with silica gel column chromatography (ethyl acetate/methanol=9/1) to obtain 12 g of a Na salt of A008.

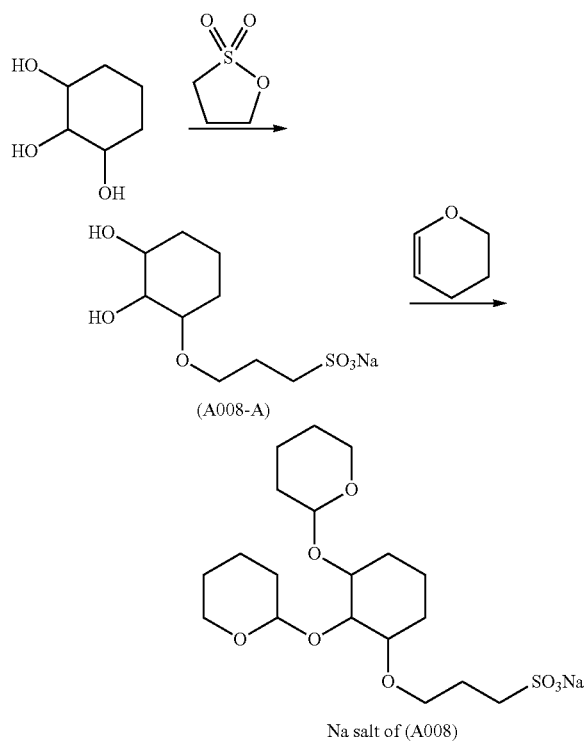

(Na Salt of A009)

13.8 g of A008-A, 55.0 g of sodium hydride (oil dispersion, a content of 60%), and 100 mL of dimethylformamide were mixed at room temperature to obtain a mixture. To the obtained mixture was added dropwise 8.1 g of chloro(methoxy)methane to obtain a reaction solution 3. The obtained reaction solution 3 was heated to 50° C., stirred for 2 hours, and then cooled to room temperature, and 5 mL of methanol was carefully added dropwise thereto to obtain a reaction solution 4. The reaction solution 4 was concentrated under reduced pressure and the obtained concentrated was purified by silica gel column chromatography (ethyl acetate/methanol=–9/1) to obtain 13.8 g of a Na salt of A009.

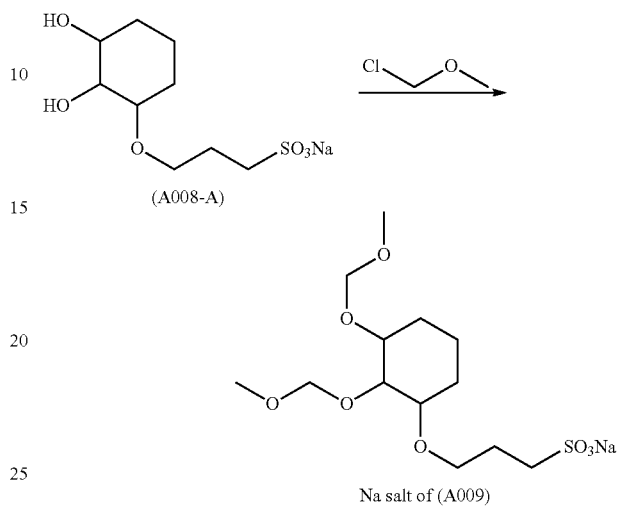

(Na Salt of A010)

A Na salt of A010 was synthesized by performing a reaction in the same manner as above, except that 2,3-dihydropyran was changed to an equimolar amount of vinyl ethyl ether in the synthesis of the Na salt of A008.

(Na Salt of A011)

A Na salt of A011 was synthesized by performing the synthesis in the same manner as above, except that 1,2,3-cyclohexanetriol as a raw material for A-008A was changed to an equimolar amount of 1,3,5-cyclohexanetriol in the synthesis of the Na salt of A009.

(Na Salt of A012)

A Na salt of A012 was obtained by performing the synthesis in the same manner as above, except that 1,2,3-cyclohexanetriol as a raw material for A-008A was changed to an equimolar amount of 1,3-cyclohexanediol and the amount of chloro(methoxy)methane was changed to a half thereof in the synthesis of the Na salt of A009.

(Na Salt of A013)

A Na salt of A013 was obtained by performing a reaction in the same manner as above, except that 1,2,3-cyclohexanetriol was changed to an equimolar amount of 2,3-norbonanediol in the synthesis of the Na salt of A008.

(Na Salt of A014)

A Na salt of A014 was obtained by performing a reaction in the same manner as above, except that 1,2,3-cyclohexanetriol was changed to an equimolar amount of tetracyclo[6.2.1.1$^{3,6}$.0$^{2,7}$]dodeca-4,5-diol in the synthesis of the Na salt of A009.

(Na Salt of A015)

A Na salt of A015 was obtained by performing a reaction in the same manner as above, except that 1,2,3-cyclohexanetriol was changed to an equimolar amount of 1,3-adamantanediol in the synthesis of the Na salt of A008.

(Na Salt of A016)

A Na salt of A016 was obtained by performing a reaction in the same manner as above, except that 1,2,3-cyclohexanetriol was changed to an equimolar amount of 1,3,5-adamantanetriol in the synthesis of the Na salt of A009.

(Na Salt of A017)

A Na salt of A017 was obtained by performing a reaction in the same manner as above, except that 1,2,3-cyclohexanetriol was changed to an equimolar amount of 1,3,5,7-adamantanetetraol and the amount of sodium hydride and chloro(methoxy)methane used in a methoxymethylating step was 1.3-fold increased in the synthesis of the Na salt of A009.

(Na Salt of A018)

A Na salt of A018 was obtained by performing a reaction in the same manner as above, except that 1,2,3-cyclohexanetriol was changed to an equimolar amount of 1,2-cyclopentanediol in the synthesis of the Na salt of A008.

<<Cationic Moiety of Photoacid Generator>>

(C001)

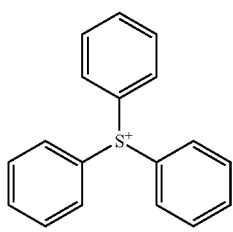

(C002)

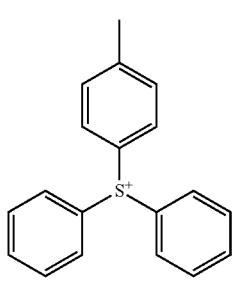

(C003)

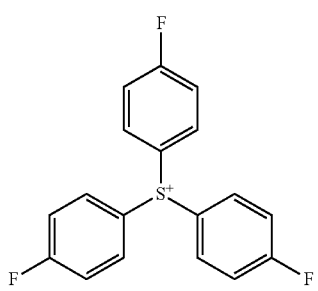

(C004)

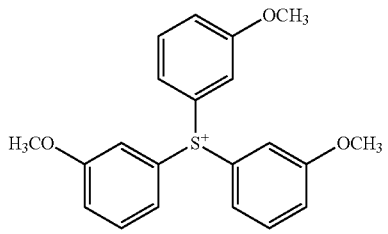

(C005)

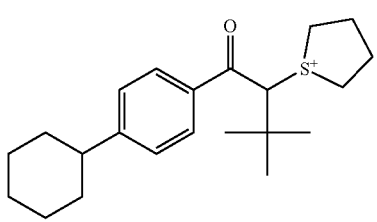

(C006)

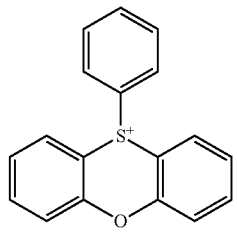

(C007)

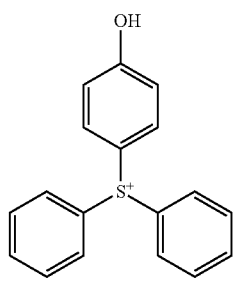

(C008)

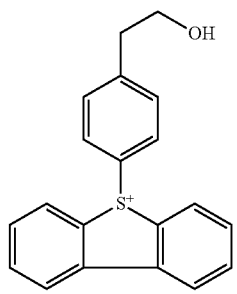

(C009)

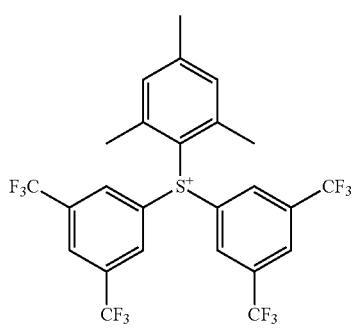

(C010)

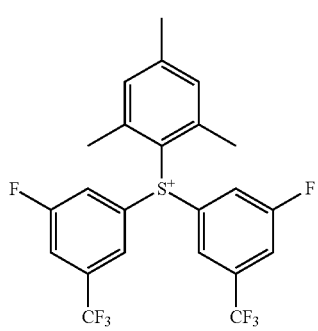

-continued

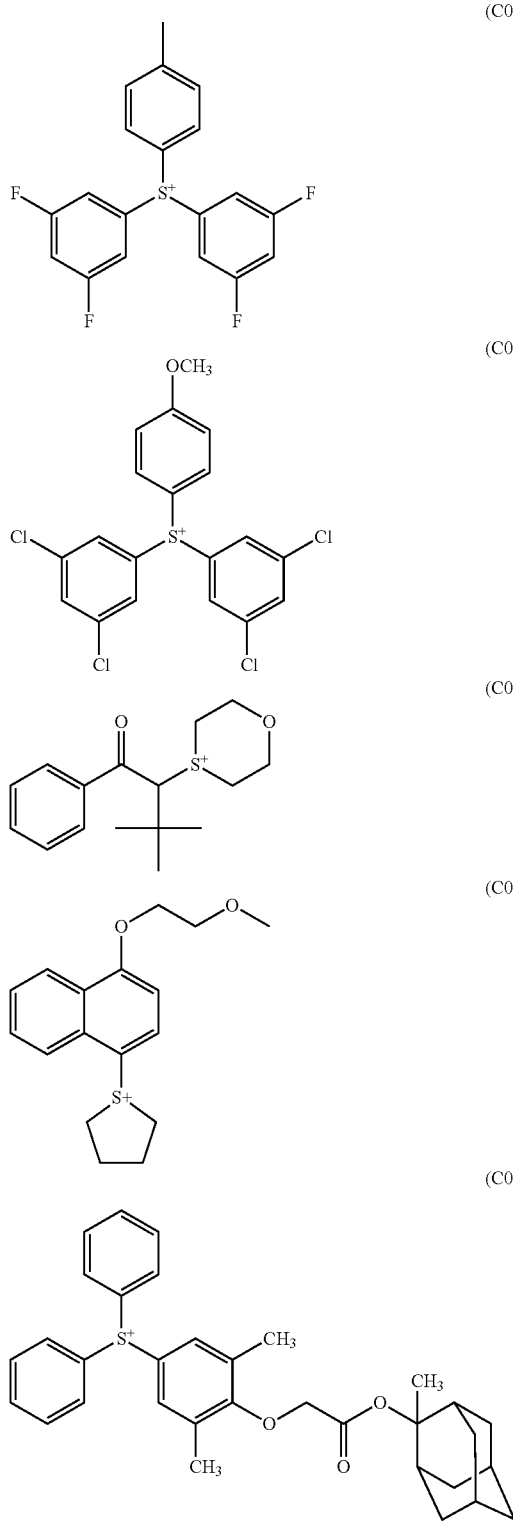

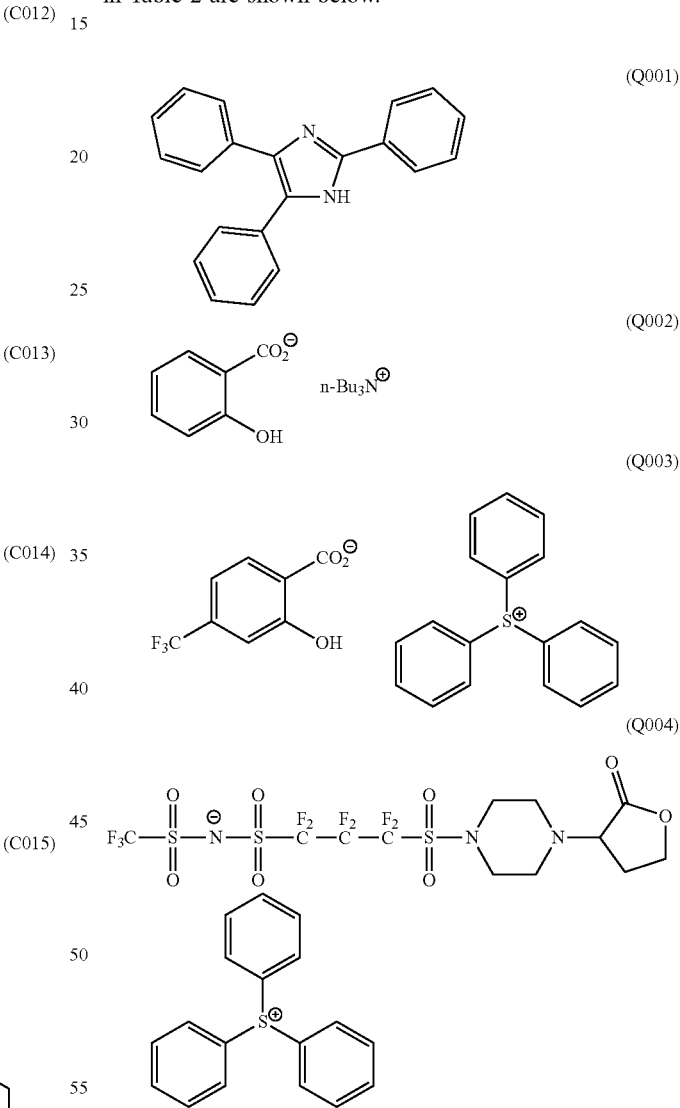

<<Synthesis Example for Photoacid Generator>>
(Photoacid Generator Formed of Anion of A002 and Cation of C002)
3.3 g of A002-Na, 2.9 g of (4-methylphenyl)diphenylsulfonium bromide, 50 mL of chloroform, and 50 mL of pure water were added to a flask and stirred for 30 minutes. After stirring, the organic layer were combined and this organic layer was washed seven times with 50 mL of pure water. The organic layer after washing was concentrated under reduced pressure to obtain 3.5 g of a photoacid generator formed of an anion of A002 and a cation of C002.
$^1$H NMR (CDCl$_3$): 7.71-7.84 (m, 12H), 6.73 (d, 2H), 4.28 (bs, 2H), 3.66 (ddd, 2H), 3.51 (5, 1H), 2.93 (ddd. 2H), 2.48 (s, 3H), 2.15 (t, 2H), 1.60-1.79 (m, 3H). 1.39-1.55 (m, 1H), 1.15-1.39 (m, 2H)

(Other Photoacid Generator)
The other photoacid generators were synthesized in the same manner as above.

<Acid Diffusion Control Agent>
The structures of the acid diffusion control agents shown in Table 2 are shown below.

<Solvent>
The solvents shown in Table 2 are shown below.
SL-1: Propylene glycol monomethyl ether acetate (PGMEA)
SL-2: Propylene glycol monomethyl ether (PGME)

<Preparation of Actinic Ray-Sensitive or Radiation-Sensitive Resin Composition>
The respective components shown in Table 2 were mixed in the addition amounts described in Table 2. Then, the obtained mixed liquid was filtered through a polyethylene filter having a pore size of 0.03 µm to prepare an actinic ray-sensitive or radiation-sensitive resin composition (hereinafter also referred to as a "resist composition"). In addition, in the resist composition, the solid content means all the components excluding the solvent. The obtained resist composition was used in Examples and Comparative Examples.

<Pattern Formation>
<<Formation of Resist Film>>

A composition for forming an underlayer film. AL412 (manufactured by Brewer Science Inc.), was applied onto a silicon wafer, and the wafer was baked at 200° C. for 60 seconds to form an underlayer film having a film thickness of 20 nm. In addition, the prepared resist composition was applied thereonto and the film was baked at 100° C. for 60 seconds to form a resist film having a film thickness of 30 nm.

<<Exposure and Development>>

The resist film was patternwise exposed through a reflective mask with a pitch of 44 nm and a line width of 22 nm, using an EUV exposure machine (manufactured by ASML; NXE3350, NA 0.33, Dipole 90o, outer sigma 0.87, inner sigma 0.35). Thereafter, the resist film was post-exposure baked (PEB) at 120° C. for 60 seconds.

Subsequently, puddle development was performed for 30 seconds using a 2.38%-by-mass aqueous tetramethylammonium hydroxide (TMAH) solution as a developer, puddle rinsing was performed 20 seconds with pure water as a rinsing liquid, and then a silicon wafer was rotated at a rotation speed of 4,000 rpm for 30 seconds to form a line-and-space resist pattern.

<Evaluation>

With regard to the resist pattern, evaluations described below were performed. The results are shown in Table 2.

<<LER>>

While changing an exposure dose, the line width of the line-and-space pattern was measured, and an exposure dose at which the line width reached 22 nm was determined and defined as an optimal exposure dose (mJ/cm$^2$).

While the line-and-space pattern resolved at the optimal exposure dose was observed from an upper part thereof with a critical dimension scanning electron microscope (SEM (CG-4100 manufactured by Hitachi High Technologies Corporation)), a distance from the center of the pattern to an edge was measured at any points and a measurement deviation thereof, 3σ, was evaluated as LER (unit: nm). A smaller value thereof indicates better performance.

<<Ability to Suppress Collapse (Ability to Suppress Pattern Collapse)>>

After forming the resist film in the same manner as above, the resist film was exposed while changing the exposure dose by 1 mJ through a mask pattern having a target size of 50 nm 1 L/1.8 S in the same manner as above. A line width (nm) of a pattern formed at an exposure dose that was 1 mJ less than an exposure dose at which line collapse was generated was measured with a critical dimension scanning electron microscope (SEM (CG-4100 manufactured by Hitachi High Technologies Corporation)), and defined as a minimum collapse dimension (nm). In addition, a smaller value thereof indicates better resistance to pattern collapse.

TABLE 2

| | Photoacid generator | | | Acid diffusion control agent | | Resin | | Solvent | | Evaluation results | |
|---|---|---|---|---|---|---|---|---|---|---|---|
| | Anion | Cation | Addition amount/g | | Addition amount/g | | Addition amount/g | Composition (mass ratio) | Addition amount/g | LER/um | Minimum collapse dimension/nm |
| Example 1 | A001 | C001 | 8 | — | — | P001 | 10 | SL-1/SL-2 (3/1) | 100 | 4.5 | 15 |
| Example 2 | A002 | C002 | 8 | — | — | P001 | 10 | SL-1/SL-2 (3/1) | 100 | 3.6 | 14 |
| Example 3 | A003 | C004 | 8 | — | — | P001 | 10 | SL-1/SL-2 (3/1) | 100 | 3.9 | 15 |
| Example 4 | A004 | C005 | 8 | — | — | P001 | 10 | SL-1/SL-2 (3/1) | 100 | 3.8 | 14 |
| Example 5 | A005 | C009 | 8 | — | — | P001 | 10 | SL-1/SL-2 (3/1) | 100 | 3.7 | 16 |
| Example 6 | A006 | C014 | 8 | — | — | P001 | 10 | SL-1/SL-2 (3/1) | 100 | 4.0 | 14 |
| Example 7 | A007 | C001 | 8 | — | — | P001 | 10 | SL-1/SL-2 (3/1) | 100 | 4.6 | 15 |
| Example 8 | A008 | C001 | 8 | — | — | P001 | 10 | SL-1/SL-2 (3/1) | 100 | 4.7 | 15 |
| Example 9 | A009 | C001 | 8 | — | — | P001 | 10 | SL-1/SL-2 (3/1) | 100 | 4.4 | 15 |
| Example 10 | A010 | C002 | 8 | — | — | P001 | 10 | SL-1/SL-2 (3/1) | 100 | 4.6 | 15 |
| Example 11 | A011 | C001 | 8 | — | — | P001 | 10 | SL-1/SL-1 (3/1) | 100 | 4.2 | 16 |
| Example 12 | A012 | C001 | 8 | — | — | P001 | 10 | SL-1/SL-2 (3/1) | 100 | 4.8 | 14 |
| Example 13 | A013 | C001 | 8 | — | — | P001 | 10 | SL-1/SL-2 (3/1) | 100 | 4.6 | 15 |
| Example 14 | A014 | C001 | 8 | — | — | P001 | 10 | SL-1/SL-2 (3/1) | 100 | 4.9 | 14 |
| Example 15 | A015 | C001 | 8 | — | — | P001 | 10 | SL-1/SL-2 (3/1) | 100 | 4.5 | 15 |
| Example 16 | A016 | C001 | 8 | — | — | P001 | 10 | SL-1/SL-2 (3/1) | 100 | 4.3 | 16 |
| Example 17 | A017 | C001 | 8 | — | — | P001 | 10 | SL-1/SL-2 (3/1) | 100 | 4.4 | 15 |
| Example 18 | A018 | C001 | 8 | — | — | P001 | 10 | SL-1/SL-2 (3/1) | 100 | 4.8 | 14 |
| Example 19 | A001 | C001 | 8 | Q001 | 5 | P001 | 10 | SL-1/SL-2 (3/1) | 100 | 3.9 | 15 |
| Example 20 | A001 | C001 | 8 | Q002 | 5 | P001 | 10 | SL-1/SL-2 (3/1) | 100 | 3.7 | 14 |
| Example 21 | A001 | C001 | 8 | Q003 | 5 | P001 | 10 | SL-1/SL-2 (3/1) | 100 | 3.3 | 14 |
| Example 22 | A001 | C001 | 8 | Q004 | 5 | P001 | 10 | SL-1/SL-2 (3/1) | 100 | 3.1 | 15 |
| Example 23 | A001 | C001 | 8 | — | — | P002 | 10 | SL-1/SL-2 (3/1) | 100 | 3.8 | 14 |
| Example 24 | A001 | C001 | 8 | — | — | P003 | 10 | SL-1/SL-2 (3/1) | 100 | 3.7 | 14 |
| Example 25 | A001 | C001 | 4 | — | — | P001 | 10 | SL-1/SL-2 (3/1) | 100 | 3.2 | 14 |
| | A002 | C002 | 4 | | | | | | | | |
| Comparative Example 1 | A901 | C001 | 8 | — | — | P001 | 10 | SL-1/SL-2 (3/1) | 100 | 7.5 | 18 |
| Comparative Example 2 | A902 | C001 | 8 | — | — | P001 | 10 | SL-1/SL-2 (3/1) | 100 | 7.0 | 19 |

Results of Comparison of Examples vs. Comparative Examples

As shown below in Table 2, the resist composition of Examples including the photoacid generator represented by General Formula (X) had better LER, as compared with the resist composition of Comparative Examples not including the photoacid generator. In addition, the resist composition of Examples also had excellent resistance to pattern collapse.

In addition, according to the comparison of Examples 1 to 18, in Examples 2 and 6 in which the photoacid generator represented by General Formula (X-1) was used and $R^{101}$ in General Formula (X-1) was an alicyclic hydrocarbon group, LER was better than in Examples 1, and 7 to 18 not satisfying such the condition.

What is claimed is:

1. An actinic ray-sensitive or radiation-sensitive resin composition comprising:
   a compound that generates an acid upon irradiation with actinic rays or radiation; and
   a resin whose polarity increases by the action of an acid, wherein the compound is represented by General Formula (X),

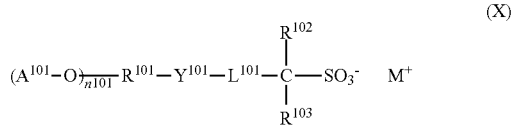

in General Formula (X),
$A^{101}$ represents a group that leaves by the action of an acid, and in a case where a plurality of $A^{101}$'s are present, the plurality of $A^{101}$'s may be linked to each other,
$n^{101}$ represents an integer of 1 to 4,
$R^{101}$ represents an ($n^{101}$+1)-valent aliphatic hydrocarbon group having no heteroatom,
$Y^{101}$ represents an ether group or an ester group,
$L^{101}$ represents a linear alkylene group having no substituent,
$R^{102}$ and $R^{103}$ each independently represents a hydrogen atom or an alkyl group having 1 to 10 carbon atom, in which a hydrogen atom is not substituted with a fluorine atom, and
$M^+$ represents a monovalent cation.

2. The actinic ray-sensitive or radiation-sensitive resin composition according to claim 1,
   wherein the compound has an acetal structure or a ketal structure in a moiety including $A^{101}$ and $R^{101}$.

3. The actinic ray-sensitive or radiation-sensitive resin composition according to claim 1,
   wherein the compound is represented by General Formula (X-1),

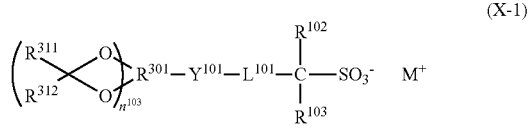

in General Formula (X-1),
$R^{311}$ and $R^{312}$ each independently represents a hydrogen atom, an alkyl group, an aryl group, a heteroaryl group, or a heterocyclic group,
$n^{301}$ represents an integer of 1 or 2,
$R^{301}$ represents an (($n^{301}$×2)+1)-valent aliphatic hydrocarbon group having no heteroatom,
$Y^{101}$ represents an ether group or an ester group,
$L^{101}$ represents a linear alkylene group having no substituent,
$R^{102}$ and $R^{103}$ each independently represents a hydrogen atom or an alkyl group having 1 to 10 carbon atom, in which a hydrogen atom is not substituted with a fluorine atom, and
$M^+$ represents a monovalent cation.

4. The actinic ray-sensitive or radiation-sensitive resin composition according to claim 3,
   wherein $R^{301}$ represents an (($n^{301}$×2)+1)-valent alicyclic hydrocarbon group having no heteroatom.

5. The actinic ray-sensitive or radiation-sensitive resin composition according to claim 1,
   wherein the compound is represented by General Formula (X-2),

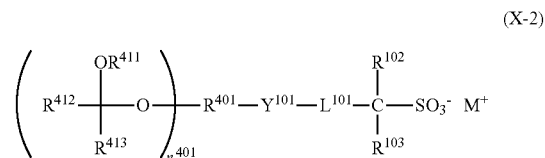

in General Formula (X-2),
R411 represents an alkyl group, an aryl group, a heteroaryl group, or a heterocyclic group,
$R^{412}$ and $R^{413}$ each independently represents a hydrogen atom, an alkyl group, an aryl group, a heteroaryl group, or a heterocyclic group,
$n^{401}$ represents an integer of 1 or 2,
$R^{401}$ represents an ($n^{401}$+1)-valent aliphatic hydrocarbon group having no heteroatom,
$Y^{101}$ represents an ether group or an ester group,
$L^{101}$ represents a linear alkylene group having no substituent,
$R^{102}$ and $R^{103}$ each independently represents a hydrogen atom or an alkyl group having 1 to 10 carbon atom, in which a hydrogen atom is not substituted with a fluorine atom, and
$M^+$ represents a monovalent cation.

6. The actinic ray-sensitive or radiation-sensitive resin composition according to claim 1,
   wherein $Y^{101}$ represents an ether group.

7. The actinic ray-sensitive or radiation-sensitive resin composition according to claim 1,
   wherein $M^+$ represents a substituted or unsubstituted triphenylsulfonium cation.

8. The actinic ray-sensitive or radiation-sensitive resin composition according to claim 1,
   wherein the resin includes a repeating unit having an acid-decomposable group,
   the acid-decomposable group has a structure with a polar group being protected with a group that leaves through decomposition by the action of an acid, and
   the polar group is a phenolic hydroxyl group.

9. The actinic ray-sensitive or radiation-sensitive resin composition according to claim 1, wherein the resin includes a repeating unit having an acid-decomposable group, the acid-decomposable group has a structure with a polar group being protected with a group that leaves through decomposition by the action of an acid, and the group that leaves through decomposition by the action of an acid is represented by Formula —C($R_{01}$)($R_{02}$)(O$R_{39}$), in the formula, $R_{39}$ represents an alkyl group, a cycloalkyl group, an aryl group, an aralkyl group, or an alkenyl group, and $R_{01}$ and $R_{02}$ each independently represents a hydrogen atom, an alkyl group, a cycloalkyl group, an aryl group, an aralkyl group, or an alkenyl group.

10. The actinic ray-sensitive or radiation-sensitive resin composition according to claim 1, further comprising a solvent.

11. A resist film formed with the actinic ray-sensitive or radiation-sensitive resin composition according to claim 1.

12. A pattern forming method comprising:
forming a resist film with the actinic ray-sensitive or radiation-sensitive resin composition according to claim 1;
exposing the resist film; and
developing the exposed resist film with a developer.

13. A method for manufacturing an electronic device, the method comprising the pattern forming method according to claim 12.

14. An actinic ray-sensitive or radiation-sensitive resin composition comprising:
a compound that generates an acid upon irradiation with actinic rays or radiation; and
a resin whose polarity increases by the action of an acid, wherein the compound is represented by General Formula (X-2),

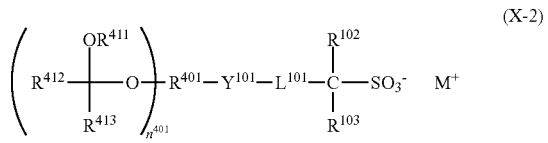

in General Formula (X-2), $R^{411}$ represents an alkyl group, an aryl group, a heteroaryl group, or a heterocyclic group, $R^{412}$ and $R^{413}$ each independently represents a hydrogen atom, an alkyl group, an aryl group, a heteroaryl group, or a heterocyclic group, $n^{401}$ represents an integer of 1 or 2, $R^{401}$ represents an ($n^{401}$+1)-valent aliphatic hydrocarbon group having no heteroatom, $Y^{101}$ represents an ether group or an ester group, $L^{101}$ represents an alkylene group, $R^{102}$ and $R^{103}$ each independently represents a hydrogen atom or an alkyl group having 1 to 10 carbon atom, in which a hydrogen atom is not substituted with a fluorine atom, and $M^+$ represents a monovalent cation.

15. The actinic ray-sensitive or radiation-sensitive resin composition according to claim 14,
wherein $M^+$ represents a substituted or unsubstituted triphenylsulfonium cation.

16. The actinic ray-sensitive or radiation-sensitive resin composition according to claim 14,
wherein the resin includes a repeating unit having an acid-decomposable group, the acid-decomposable group has a structure with a polar group being protected with a group that leaves through decomposition by the action of an acid, and the polar group is a phenolic hydroxyl group.

17. The actinic ray-sensitive or radiation-sensitive resin composition according to claim 14,
wherein the resin includes a repeating unit having an acid-decomposable group, the acid-decomposable group has a structure with a polar group being protected with a group that leaves through decomposition by the action of an acid, and the group that leaves through decomposition by the action of an acid is represented by Formula —($R_{01}$)($R_{02}$)(O$R_{39}$), in the formula, $R_{39}$ represents an alkyl group, a cycloalkyl group, an aryl group, an aralkyl group, or an alkenyl group, and $R_{01}$ and $R_{02}$ each independently represents a hydrogen atom, an alkyl group, a cycloalkyl group, an aryl group, an aralkyl group, or an alkenyl group.

18. An actinic ray-sensitive or radiation-sensitive resin composition comprising:
a compound that generates an acid upon irradiation with actinic rays or radiation; and
a resin whose polarity increases by the action of an acid, wherein the compound is represented by General Formula (X),

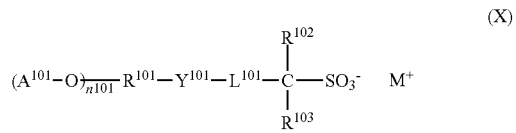

in General Formula (X), $A^{101}$ represents a group that leaves by the action of an acid, and in a case where a plurality of $A^{101}$'s are present, the plurality of $A^{101}$'s may be linked to each other, $n^{101}$ represents an integer of 1 to 4, $R^{101}$ represents an ($n^{101}$+1)-valent aliphatic hydrocarbon group having no heteroatom, $Y^{101}$ represents an ether group, $L^{101}$ represents an alkylene group, $R^{102}$ and $R^{103}$ each independently represents a hydrogen atom or an alkyl group having 1 to 10 carbon atom, in which a hydrogen atom is not substituted with a fluorine atom, and $M^+$ represents a monovalent cation.

19. The actinic ray-sensitive or radiation-sensitive resin composition according to claim 18,
wherein $M^+$ represents a substituted or unsubstituted triphenylsulfonium cation.

20. The actinic ray-sensitive or radiation-sensitive resin composition according to claim 18,
wherein the resin includes a repeating unit having an acid-decomposable group, the acid-decomposable group has a structure with a polar group being protected with a group that leaves through decomposition by the action of an acid, and the polar group is a phenolic hydroxyl group.

21. The actinic ray-sensitive or radiation-sensitive resin composition according to claim 18,
wherein the resin includes a repeating unit having an acid-decomposable group, the acid-decomposable group has a structure with a polar group being protected with a group that leaves through decomposition by the action of an acid, and the group that leaves through decomposition by the action of an acid is represented by Formula —$(R_{01})(R_{02})(OR_{39})$, in the formula, $R_{39}$ represents an alkyl group, a cycloalkyl group, an aryl group, an aralkyl group, or an alkenyl group, and $R_{01}$ and $R_{02}$ each independently represents a hydrogen atom, an alkyl group, a cycloalkyl group, an aryl group, an aralkyl group, or an alkenyl group.

* * * * *